United States Patent
Pradella et al.

(10) Patent No.: US 11,162,116 B2
(45) Date of Patent: Nov. 2, 2021

(54) METHODS FOR THE CO-PRODUCTION OF ETHYLENE GLYCOL AND THREE CARBON COMPOUNDS

(71) Applicant: Braskem S.A., Sao Paulo (BR)

(72) Inventors: Jose Geraldo Da Cruz Pradella, Campinas (BR); Ane Fernanda Beraldi Zeidler, Campinas (BR); Ana Karina Brambilla Costa, Campinas (BR)

(73) Assignee: BRASKEM S.A., Camacari (BR)

( * ) Notice: Subject to any disclaimer, the term of this patent is extended or adjusted under 35 U.S.C. 154(b) by 45 days.

(21) Appl. No.: 16/351,137

(22) Filed: Mar. 12, 2019

(65) Prior Publication Data
US 2019/0276858 A1 Sep. 12, 2019

Related U.S. Application Data
(60) Provisional application No. 62/641,830, filed on Mar. 12, 2018.

(51) Int. Cl.
| | | |
|---|---|---|
| *C12P 7/28* | (2006.01) | |
| *C12P 7/04* | (2006.01) | |
| *C12P 7/18* | (2006.01) | |
| *C12N 1/20* | (2006.01) | |

(52) U.S. Cl.
CPC .............. *C12P 7/18* (2013.01); *C12N 1/20* (2013.01); *C12P 7/28* (2013.01); *C12N 2500/34* (2013.01)

(58) Field of Classification Search
CPC .................................. C12P 7/18; C12P 5/026
See application file for complete search history.

(56) References Cited

U.S. PATENT DOCUMENTS

| | | | |
|---|---|---|---|
| 2015/0284692 | A9 | 8/2015 | Koepke et al. |
| 2017/0260551 | A1 | 9/2017 | Koch et al. |
| 2019/0323016 | A1* | 10/2019 | Lopes .................. C12N 9/0006 |

OTHER PUBLICATIONS

Zhang et al., "Production of C2-C4 diols from renewable bioresources: new metabolic pathways and metabolic engineering strategies," Biotechnology for Biofeuls, vol. 10, No. 299, Dec. 13, 2017 (Dec. 13, 2017), pp. 1-20.
Sun et al., "Synthesis of Chemicals by Metabolic Engineering of Microbes," Chemical Society Reviews, vol. 44, No. 11, Jun. 7, 2015 (Jun. 7, 2015), pp. 3760-3785.
International Search Report and Written Opinion for Application No. PCT/US19/21905, dated May 10, 2019, 9 pages.
International Preliminary Report on Patentability for Application No. PCT/US19/21905, dated Sep. 15, 2020, 8 pages.

* cited by examiner

*Primary Examiner* — Maryam Monshipouri
(74) *Attorney, Agent, or Firm* — Morgan, Lewis & Bockius LLP

(57) ABSTRACT

The present disclosure relates to single and/or multi-stage, biological processes and systems for converting C5, C6, and/or disaccharide carbon sources to desirable products including monoethylene glycol (MEG) and one or more three-carbon compounds such as acetone, isopropanol or propene. The MEG and one or more three-carbon compounds described herein are useful as starting material for production of other compounds or as end products for industrial and household use. The disclosure further relates to the processes carrying out fermentations of substrates in a single phase bioreactor or in a multiphase bioreactor comprising growth and production phases. Additionally, the processes and systems described herein result in high productivity and yield of the desired products due to intermittent or continuous removal of products to avoid inhibitory effects.

17 Claims, 9 Drawing Sheets

METHODS FOR THE CO-PRODUCTION OF ETHYLENE GLYCOL AND THREE CARBON COMPOUNDS

CROSS-REFERENCE TO RELATED APPLICATIONS

This application claims the benefit of priority to U.S. Provisional Application No. 62/641,830, filed Mar. 12, 2018; which is herein incorporated by reference in its entirety.

TECHNICAL FIELD

The present disclosure relates to biological processes and systems for converting C5 and/or C6 carbon sources to desired products by microbial fermentation. The present application also relates to the processes and systems utilizing single and/or multiple bioreactor stage(s) to produce monoethylene glycol (MEG) and one or more three-carbon compounds such as acetone, isopropanol, or propene with high simultaneous yield and productivity.

BACKGROUND

Organic compounds such as monoethylene glycol (MEG), and the C3 compounds acetone (ACE), isopropanol (IPA), and propene are valuable as raw material for the production of materials such as polyethylene terephthalate (PET), resins from MEG, and the plastic polypropylene from propene. These organic compounds are directly used for industrial or household purposes.

However, the compounds are currently produced from precursors that originate from fossil fuels, which contribute to climate change. Due to environmental concerns over fossil fuel greenhouse gas emissions, emphasis on renewable energy sources has been globally increased. To keep pace with global requirements, academia and industry has drawn attention to the development of more environment-friendly renewable raw material. While researchers have engineered microorganisms with biosynthetic pathways to produce MEG or IPA separately, these pathways are challenging mainly due to loss of product yield and redox balance, which are some obstacles to overcome. Also, a large volume of recombinant microorganisms in a bioreactor cause another challenge of removal of excessive biomolecules produced during the production of end products.

Thus, there is an unmet need for improved biological processes and systems for the simultaneous production of MEG and three-carbon compounds such as ACE, IPA and propene in a single and/or multiple bioreactor(s) in an efficient, economic, environmentally friendly, and consistent manner.

SUMMARY OF THE DISCLOSURE

The present application relates to methods of co-producing monoethylene glycol and one or more C3 compounds.

In one aspect, the present disclosure provides a biological process for producing two or more desirable products simultaneously, the process comprising (a) providing to at least one bioreactor one or more recombinant microorganisms engineered to express one or more enzymes from one or more biosynthesis pathways selected from a monoethylene glycol (MEG) biosynthesis pathway and one or more C3 compound biosynthesis pathways; (b) cultivating the one or more recombinant microorganisms from (a) in one or more stages in a culture medium containing a feedstock comprising one or more substrates comprising C5 carbohydrates, C6 carbohydrates, and/or disaccharides; (c) fermenting the culture in one or more stages under aerobic, microaerobic and/or anaerobic conditions; and (d) recovering from the bioreactor MEG and at least one second desirable product from (c) selected from the group consisting of acetone, isopropanol, propene, precursors thereof, and mixtures thereof; wherein the at least one second desirable product is recovered continuously prior to exhaustion of the one or more substrates.

In one aspect, the present disclosure provides a biological process for producing two or more desirable products simultaneously, the process comprising: (a) providing to a bioreactor one or more recombinant microorganisms engineered to express one or more enzymes from one or more biosynthesis pathways selected from a monoethylene glycol (MEG) biosynthesis pathway and one or more C3 compound biosynthesis pathways; (b) cultivating the recombinant microorganism from (a) in one or more stages in a culture medium containing a feedstock comprising one or more substrates comprising C5 carbohydrates, C6 carbohydrates, and/or disaccharides; (c) fermenting the culture in one or more stages under aerobic, microaerobic and/or anaerobic conditions; and (d) recovering from the bioreactor the MEG and at least one second desirable product from (c) selected from the group consisting of acetone, isopropanol, propene, precursors thereof, and mixtures thereof; wherein the at least one second desirable product is recovered from the bioreactor two or more times prior to exhaustion of the one or more substrates.

In one aspect, the present disclosure provides a process for producing two or more desirable products simultaneously, the process comprising: (a) providing to a bioreactor one or more recombinant microorganisms engineered to express one or more enzymes from one or more biosynthesis pathways selected from a monoethylene glycol (MEG) biosynthesis pathway and one or more C3 compound biosynthesis pathways; (b) cultivating the one or more recombinant microorganisms from (a) in one or more stages in a culture medium containing a feedstock comprising one or more substrates comprising C5 carbohydrates, C6 carbohydrates, and/or disaccharides; (c) fermenting the culture in one or more stages under aerobic, microaerobic and/or anaerobic conditions; and (d) recovering from the bioreactor MEG and at least one second desirable product from (c) selected from the group consisting of acetone, isopropanol, propene, precursors thereof, and mixtures thereof; wherein the at least one second desirable product is recovered from the bioreactor continuously prior to exhaustion of the one or more substrates; and wherein (b) and (c) occur together in the same stage.

In one aspect, the present disclosure provides a process for producing two or more desirable products simultaneously, the process comprising: (a) providing to a bioreactor one or more recombinant microorganisms engineered to express one or more enzymes from one or more biosynthesis pathways selected from a monoethylene glycol (MEG) biosynthesis pathway and one or more C3 compound biosynthesis pathways; (b) cultivating the one or more recombinant microorganisms from (a) in one or more stages in a culture medium containing a feedstock comprising one or more substrates comprising C5 carbohydrates, C6 carbohydrates, and/or disaccharides; (c) fermenting the culture in one or more stages under aerobic, microaerobic and/or anaerobic conditions; and (d) recovering from the bioreactor in one or more stages MEG and at least one second desirable product from (c) selected from the group consisting of acetone, isopropanol, propene, precursors thereof, and mixtures thereof; wherein the at least one second desirable product is recovered from the bioreactor continuously prior to exhaustion of the one or more substrates; and wherein (b) and (c) occur in separate stages.

In some aspects, the one or more recombinant microorganisms are engineered to express at least one enzyme selected from the group consisting of: D-tagatose 3-epimerase, D-ribulokinase D-ribulose-1-phosphate aldolase, glycolaldehyde reductase, thiolase, acetate:acetoacetyl-CoA transferase, acetoacetate decarboxylase, D-xylulose 1-kinase, D-xylulose-1-phosphate aldolase, xylose isomerase, xylose reductase, xylitol dehydrogenase, xylose dehydrogenase, xylonolactonase, xylonate dehydratase, 2-keto-3-deoxy-D-pentonate aldolase, secondary alcohol dehydrogenase, dehydratase, and a functionally equivalent variant of any one or more thereof.

In further aspects, the one or more recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis* and *Terrisporobacter glycolicus*.

In some aspects, the one or more recombinant microorganisms are acetogenic.

In some aspects, the one or more C3 compound biosynthesis pathways are selected from the group consisting of: an acetone biosynthesis pathway, an isopropanol biosynthesis pathway, and a propene biosynthesis pathway. In some aspects, the one or more substrates are C5 carbohydrates selected from the group consisting of xylose, arabinose, lyxose, ribose, ribulose, and xylulose. In some aspects, the one or more substrates are C6 carbohydrates selected from the group consisting of glucose, mannose, fructose, allose, gulose, idose, galactose, talose, sorbose, tagatose, and psicose. In some aspects, the one or more substrates are disaccharides selected from the group consisting of sucrose, lactose, lactulose, maltose, trehalose, cellobiose, and chitobiose. In some aspects, the one or more substrates comprise C5 carbohydrates and C6 carbohydrates in a ratio of 20:1 to 1:20.

In some aspects, the one or more desired products is selected from the group consisting of MEG, acetone, isopropanol, and propene.

In some aspects, the cultivating and fermenting steps occur in the same stage. In some aspects the cultivating and fermenting steps occur in separate stages. In some aspects, the cultivating and fermenting steps occur in separate bioreactors. In some aspects, the cultivating and fermenting steps occur in the same bioreactor.

In some aspects, the bioreactor operates under aerobic, microaerobic, or anaerobic conditions; or a combination thereof. In some aspects, a first stage of the cultivation operates under aerobic or microaerobic conditions, and any subsequent stages operate under aerobic, microaerobic, or anaerobic conditions.

In some aspects, the one or more stages of the fermentation step receive the culture and/or culture media as a batch, a fed-batch, or a continuous mode feed. In some aspects, the cultivating stage receives the culture and/or culture media as a batch, a fed-batch, or a continuous mode feed, and any subsequent stages operate as a batch, a fed-batch, or a continuous mode feed. In some aspects, the cultivation step occurs in a different type of bioreactor than the subsequent step. In some aspects, the cultivation steps occurs in the same type of bioreactor as the subsequent step.

In some aspects, an additional feedstock comprising a gaseous substrate is provided to the bioreactor. In some aspects, the gaseous substrate comprises hydrogen gas, carbon monoxide, carbon dioxide, or combinations thereof.

In some aspects, the acetone, isopropanol, and/or propene are produced, and wherein said acetone, isopropanol, and/or propene, or a mixture thereof are recovered from the bioreactor continuously in situ.

In some aspects, the cultivation step occurs prior to the fermentation step. In some aspects, the cultivation step and the fermentation step occur concurrently.

In some aspects, the at least one second desirable product recovered is acetone and/or isopropanol. In some aspects, acetone, isopropanol, and/or MEG, in total, are produced in an amount of at least about 2 $kg/m^3$ per hour. In some aspects, a concentration of acetone, isopropanol, and/or MEG produced is at least about 40 g/L.

In some aspects, the oxygen concentration in the cultivating step is adjusted to a range of 1% to 50% of oxygen dissolved in the medium. In some aspects, the total amount of the one or more substrates that are provided to the cultivating step ranges from about 10 $kg/m^3$ to about 500 $kg/m^3$.

In some aspects, the culture medium comprises carbon (C) that is provided from C5 carbohydrates, C6 carbohydrates, and/or disaccharides. In some aspects, the culture medium comprises essential nutrients including nitrogen (N), phosphorous (P), magnesium (Mg), and iron (Fe). In some aspects, the ratio of C:N in the cultivating step is at least 10:1. In some aspects, the ratio of C:P in the cultivating step is at least 5:1. In some aspects, the ratio of C:Mg in the cultivating step is at least 50:1. In some aspects, the ratio of C:Fe in the cultivating step is at least 300:1

In some aspects, the final concentration of cell mass of the one or more recombinant microorganisms in the cultivating step ranges from about 1 $kg/m^3$ to about 100 $kg/m^3$ as of a dry cell mass. In some aspects, the cultivating step operates from 5 up to 100 hours for the cultivation of the cells of the one or more recombinant microorganism.

In some aspects, the culture in the fermenting step comprises about 1% to about 30% of the cell mass, which is transferred from the cultivating step in the culture medium with the one or more substrates. In some aspects, the oxygen concentration in the fermenting step is adjusted to a range of 0% to 10% of dissolved oxygen in the medium. In some aspects, the total amount of the one or more substrates that are provided to the fermenting step ranges from about 100 $kg/m^3$ to about 800 $kg/m^3$.

In some aspects, the ratio of C:N in the fermenting step is at least 50:1. In some aspects, the ratio of C:P in the fermenting step is at least 20:1. In some aspects, the ratio of C:Mg in the fermenting step is at least 200:1. In some aspects, the ratio of C:Fe in the fermenting step is at least 800:1. In some aspects, the fermenting step operates from 10 up to 300 hours for fed-batch operation and up to 300 hours for continuous operation.

In some aspects, the total amount of the one or more substrates that are provided to the bioreactor ranges from about 100 kg/m$^3$ to about 800 kg/m$^3$. In some aspects, the ratio C:N in the bioreactor is at least 10:1. In some aspects, the ratio of C:P in the fermenting step is at least 5:1. In some aspects, the ratio of C:Mg in the fermenting step is at least 50:1. In some aspects, the ratio of C:Fe in the fermenting step is at least 300:1. In some aspects, the fermenting step operates between 10 and 300 hours.

In some aspects, the desirable products that are recovered from the fermenting step are acetone, isopropanol, MEG, and/or propene. In some aspects, acetone is produced at least about 20 kg/m$^3$. In some aspects, isopropanol is produced at least about 35 kg/m$^3$. In some aspects, MEG is produced at least about 100 kg/m$^3$. In some aspects, the acetone and/or isopropanol is removed from the fermentation broth in situ. In some aspects the three or more desirable products are produced simultaneously.

BRIEF DESCRIPTION OF DRAWINGS

Illustrative embodiments of the disclosure are illustrated in the drawings, in which.

DETAILED DESCRIPTION

Definitions

Figure 1:
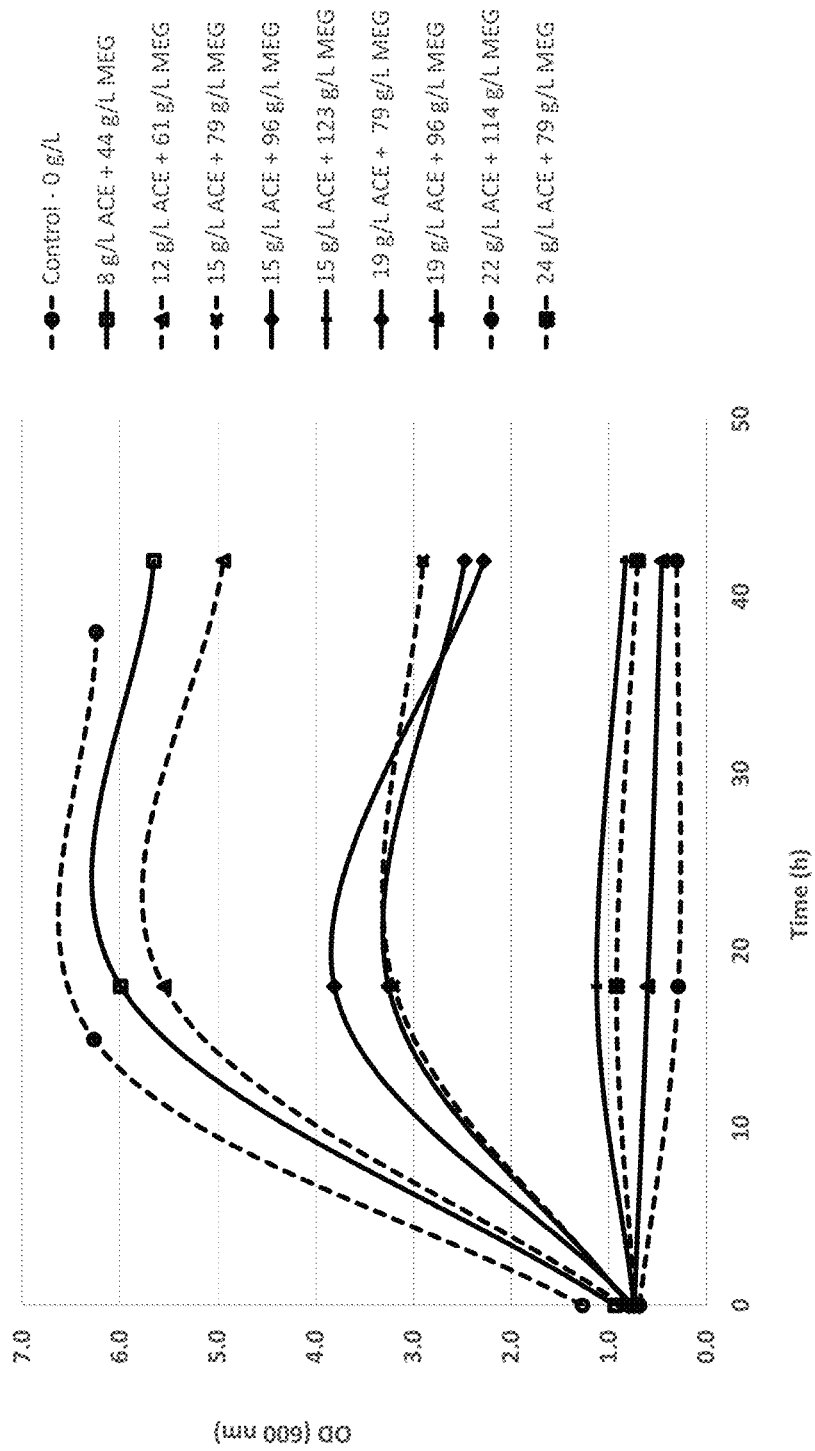
FIG. 1 illustrates the tolerance of *E. coli* grown in culture media with increasing values of acetone (ACE) and MEG.

The following definitions and abbreviations are to be used for the interpretation of the disclosure.

As used herein and in the appended claims, the singular forms "a," "an," and "the" include plural referents unless the context clearly dictates otherwise. Thus, for example, reference to "a three-carbon compound" includes a plurality of such three-carbon compounds and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukaryota, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganisms. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacilli, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) *Spirochetes* and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacil-* lus, *Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

As used herein, the term "anaerobic" when used in reference to a culture or growth condition is intended to mean that the amount of oxygen is less than about 0% of saturation for dissolved oxygen in liquid media. The term also is intended to include sealed chambers of liquid or solid media maintained with an atmosphere of less than about 0% oxygen.

As used herein, the term "aerobic" when used in reference to a culture or growth condition is intended to mean that the amount of oxygen is greater than about 10% of saturation for dissolved oxygen in liquid media. The term is also intended to include sealed chambers of liquid or solid media maintained with an atmosphere of about 10% oxygen to about 21% oxygen (as found in the atmosphere at sea level).

As used herein, the term "microaerobic" when used in reference to a culture or growth condition is intended to mean that the amount of oxygen is present in subsaturating amounts between anaerobic and aerobic conditions, wherein aerophilic microorganisms are capable of being sustained without an anoxic die off of the aerophilic microorganisms, the term "microaerobic" when used in reference to a culture or growth condition is intended to mean that the amount of oxygen is between 0% and 10% of saturation for dissolved oxygen in liquid media. The term is also intended to include sealed chambers of liquid or solid media maintained within a flow of oxygen that is utilized at about the same rate as it is provided without achieving aerobic conditions.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotide oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the poly peptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the enzyme.

The term "yield potential" as used herein refers to a yield of a product from a biosynthetic pathway. In one embodiment, the yield potential may be expressed as a percent by mass of end product per mass of starting compound.

The term "thermodynamic maximum yield" as used herein refers to the maximum yield of a product obtained from fermentation of a given feedstock, such as glucose or xylose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

The terms "C2 pathway", "C2 branch pathway" or "C2 stream" as used herein refers to a biochemical pathway wherein MEG can be produced via glycoaldehyde.

The terms "C3 pathway", "C3 branch pathway" or "C3 stream" as used herein refers to a biochemical pathway wherein Acetone, IPA, or one or more three-carbon compounds can be produced via pyruvate or dihydroxyacetone-phosphate (DHAP).

As used herein, the term "biocatalyst" refers to a substance, such as an enzyme or hormone that initiates or increases the rate of a biological, chemical, or biocatalytic reaction. In some embodiments of the present disclosure, the biocatalysts such as protein enzymes and/or hormones from microorganisms perform chemical transformations on organic compounds in fermentation process.

As used herein, the term "bioproduct", "end product" or "desired product" refers to a fermentation product of interest, typically to the fermentation product of highest concentration in a fermentation broth.

The term "bioreactor," as well as any bioreactor that may be included as part of a "bioreactor stage," is not limited to a circulated loop reactor, but more broadly includes any suitable vessel, or section within a vessel, for maintaining a liquid volume of culture medium with carboxydotrophic microorganism that may be used to carry out the biological processes described herein, which may also be referred to as fermentation processes to the extent that they are generally conducted anaerobically. Particular types of bioreactors can include any vessels suitable for two-phase (gas-liquid) contacting, for example counter-current flow reactors (e.g., with an upwardly-flowing vapor phase and downwardly-flowing liquid phase) or co-current flow reactors (e.g., with upwardly-flowing gas and liquid phases). In such two-phase contacting vessels, it is possible for the liquid phase to be the continuous phase, as in the case of gas bubbles flowing through a moving column of liquid. Otherwise, it is possible for the vapor phase to be the continuous phase, as in the case of a dispersed liquid (e.g., in the form of droplets) flowing through a vapor space. In some embodiments, described more fully below, different zones of a bioreactor may be used to contain a continuous liquid phase and a continuous gas phase. The bioreactor includes a fermentation device consisting of one or more vessels and/or towers or piping arrangement, which includes the Continuous Stirred Tank Bioreactor, Bubble Column Bioreactor, Airlift Bioreactor, Fluidized Bed Bioreactor. Packed Bed Bioreactor. Photo-Bioreactor, Immobilized Cell Reactor, Trickle Bed Reactor, Moving Bed Biofilm Reactor. Bubble Column, Gas Lift Fermenter, Membrane Reactors such as Hollow Fiber Membrane Bioreactor, or other vessel or other device suitable for gas-liquid contact. Suitable bioreactors may include static mixers, or other vessels and/or devices (e.g., towers or piping arrangements), suitable for contacting the substrate with the liquid bacterial culture medium (e.g., with dissolution and mass transport kinetics favorable for carrying out the biological conversion). The phrases "plurality of bioreactors" or bioreactors that may be included in a "plurality of bioreactor stages" are meant to include bioreactors of more than a single type, although in some cases the plurality of bioreactors may be of one type (e.g., circulated loop reactors). In some embodiments the bioreactor may comprise a first growth (propagation) reactor and a second fermentation reactor. In other embodiments the bioreactor may comprise a reactor(s) and stage(s) for both growth (propagation) and fermentation processes, which may occur together or separately. The growth or propagation phase is also known as the cultivation phase. The fermentation phase is also known as the production phase. As such, when referring to the addition of substrate to the bioreactor or fermentation reaction it should be understood to include addition to either or both of these reactors where appropriate. In some embodiments, the bioreactor(s) comprise a single stage, two stages, three stages, four stages, five stages, six stages, seven stages, eight stages, nine stages or ten stages. In some embodiments, the bioreactor(s) comprise at least one stage, at least two stages, at least three stages, at least four stages, at least five stages, at least six stages, at least seven stages, at least eight stages, at least nine stages or at least ten stages.

As referred to herein, a "broth bleed" is the portion of the fermentation broth removed from a bioreactor that is not passed to a separator.

As referred to herein, a "broth culture" is a microorganism culture present in the fermentation broth.

As referred to herein, a "broth culture density is the density of microorganism cells in the fermentation broth.

As referred to herein, a "culture medium/media" or a "nutrient medium/media" is a solution added to the fermentation broth containing nutrients and other components appropriate for the growth of the microorganism culture. In some embodiments, a minimum define culture/nutrient medium is utilized. In some embodiments, a complex undefined medium is utilized.

As referred to herein, a "dilution rate" is a rate of replacement of the broth in a bioreactor. The dilution rate is measured in the number of bioreactor volumes of broth that are replaced by nutrient medium per day.

As used herein, the term "feedstock" refers to at least one carbon source for fermentation to produce the desired product(s). A feedstock is defined as any renewable, biological material that can be used directly as a fuel, or converted to another form of fuel or energy product. Biomass feedstocks are the plant and algal materials used to derive fuels like ethanol, butanol, biodiesel, and other hydrocarbon fuels. Examples of biomass feedstocks include corn starch, sugarcane juice, crop residues such as corn stover and sugarcane bagasse, purpose-grown grass crops, and woody plants. In some embodiments, the feedstock described herein comprises C5 and/or C6 carbohydrates. In some embodiments the feedstock is supplemented with exogenous C5 and/or C6 carbohydrates. In some embodiments the feedstock comprises lignocellulosic biomass. In some embodiments the feedstock comprises cellulosic biomass. In some embodiments the feedstock comprises plant biomass. In some embodiments the feedstock comprises syngas or gaseous mixtures of $CO_2$, CO, and $H_2$. In some embodiments, the feedstock comprises a biomass that is further supplemented with one or more exogenous carbon sources. In some embodiments, a feedstock may comprise a hydrolysate of plant, human, fungal, or artificial origin.

The term "fermenting". "fermentation process" or "fermentation reaction" and the like, as used herein, are intended to encompass the growth phase and/or product biosynthesis phase of the process. As will be described further herein, in some embodiments the bioreactor may comprise a first growth (propagation phase) reactor and a second (product biosynthesis phase) fermentation reactor. In other embodiments the bioreactor may comprise a reactor for both growth (propagation) and production process. As such, the addition of elements or compositions to a fermentation reaction should be understood to include addition to either or both of these reactors or phases.

As referred to herein, a "fermentation broth" is a culture medium comprising at least a nutrient media and microorganisms.

The terms "increasing the efficiency", "increased efficiency" and the like, when used in relation to a fermentation process, include, but are not limited to, increasing one or more of the rate of growth of microorganisms catalyzing the fermentation, the growth and/or product production rate at elevated concentrations of desired products including MEG, and one or more three-carbon compounds such as acetone, isopropanol and/or propene, the volume of desired product produced per volume of substrate consumed, the rate of production or level of production of the desired product, the relative proportion of the desired product produced compared with other by-products of the fermentation and the yield of production of the desired products.

The term "industrial waste or off gases" should be taken broadly to include any gases produced by an industrial process and include gases produced as a result of ferrous metal products manufacturing, non-ferrous products manufacturing, petroleum refining processes, gasification of coal, gasification of biomass, electric power production, black production, and coke manufacturing.

As referred to herein, a "permeate" is a substantially soluble constituent of the broth that pass through a separator and are not retained by the separator. The permeate will typically contain soluble fermentation products, by-products, and nutrient solutions.

As used herein, the term "productivity" refers to the total amount of bioproduct produced per hour.

As referred to herein, a "separator" is a module that is adapted to receive fermentation broth from a bioreactor and pass the broth through a filter to yield a retentate and a permeate. The filter may be a membrane, e.g. cross-flow membrane or a hollow fiber membrane.

The term "storage" or "store" are used herein to periods when a microbial culture has a limited substrate supply or a substrate is unavailable. As such, the term includes periods when a microbial culture under steady state growth conditions is temporarily unavailable limited in substrate supply and includes periods when a microbial culture is transferred from a bioreactor into a storage vessel, such as an inoculum transfer vessel.

The term "sugar" refers to carbohydrates having 5 to 12 carbon atoms and includes, but is not limited to, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, sucrose, D-fructose, D-mannose, L-mannose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEIHU).

The present disclosure generally relates to a fermentative process to simultaneously produce MEG, and one or more other C3 molecules such as acetone (ACE), isopropanol (IPA), and propene from typical C5 carbohydrates (pentose-_such as xylose, arabinose, etc.), and C6 carbohydrates derived from biomass (hexose such as glucose, mannose, fructose, etc.), and disaccharides such as sucrose, lactose, lactulose, maltose, trehalose, cellobiose, and chitobiose. Moreover, the process uses a recombinant *E. coli* cultivated in a bioreactor with simultaneous removal of the produced biomolecules, in order to alleviate product inhibition due to its accumulation in the culture media. Thus, the present disclosure teaches obtaining a much more efficient process of producing MEG and one or more C3 compounds described herein than other processes well known to those of ordinary skill in the art. See, for example, International Patent Application Publication No. WO/2016/079440 and U.S. Patent Application Publication No. US20150147794, each of which is expressly incorporated herein by reference in their entirety.

In some embodiments, the present disclosure teaches that the use of the biological processes and systems for the production of bioproducts and/or desired products taught herein leads to combined productivity of MEG, ACE and IPA superior to 1 $kg/m^3$ h; high product concentration above 40 g/L; and product yields above 50% of theoretical value.

Culture Medium

For growth of the microorganisms, a suitable liquid nutrient medium is fed to the bioreactor. A nutrient medium will contain vitamins and minerals sufficient to permit growth of the microorganisms. Anaerobic media suitable for the fermentation of acetate and/or like products using $CO_2$ as the sole carbon source are known in the art. For example, suitable media are described in U.S. Pat. Nos. 5,807,722 and 6,340,581, and the tables herein.

In some embodiments, the media is maintained under conditions dictated by the type of microorganisms being grown. Media conditions considered include pressure, temperature, gas flow rate, liquid flow rate, pH, media redox potential, agitation rate, inoculum level, maximum gas substrate ($CO_2$, $O_2$, CO, $H_2$) concentrations, and maximum product concentrations.

In some embodiments, the nutrient medium is fed to a single stage of the bioreactor. In some embodiments, the nutrient medium is fed to two or more stages of the bioreactor. In some embodiments, the nutrient medium is fed continuously to the bioreactor. In some embodiments, the microorganisms are cultured in a first medium to maximize concentration or colony forming units per unit of media volume, and then the first culture is added to a bioreactor comprising a second medium, wherein the first medium and second medium are distinct from one another. In some embodiments, the first medium is formulated for maximum microorganism growth. In some embodiments, the second medium is formulated for maximum production of a product of interest. In some embodiments the first and second medium may be equal in volume and/or solute concentration. In some embodiments, there is more than one stage of the bioreactor for maximizing concentration or colony forming per unit of media volume.

In some embodiments the culture media may be fed to the bioreactors in the following mode of operation of bioreactors: batch, fed-batch without or with cell recycle, constant fed-batch, exponential fed-batch, linear fed-batch, repeated fed-batch known as "fill and draw" procedure, continuous without cell recycle, continuous with cell recycle including immobilized cell by various methods.

In some embodiments, the culture media used in the process described herein comprises a minimal media (MM) supplied with C5 carbohydrates, such as xylose and arabinose and C6 carbohydrates such as glucose, mannose and fructose. The culture media MM contains C5 carbohydrates, C6 carbohydrates, and/or disaccharides. In some embodiments, C5 and C6 carbohydrates in a proportion can be varied in the range of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:10, 1:15 and 1:20. In other embodiments, C5 and C6 carbohydrates in a proportion can be in the range of 6:1 to 1:6. In other embodiments, C5 or C6 carbohydrates can be used solely as a carbon source. In further embodiments, essential nutrients are included in the culture media and proportions of essential nutrients vary depending on the modes of the fermentative process such as one-phase process and/or two-phase process.

In some embodiments, one or more substrates are C5 carbohydrates. In further embodiments, the C5 carbohydrates are selected from the group consisting of xylose, arabinose, lyxose, ribose, ribulose, and xylulose. In some embodiments, one or more substrates are C6 carbohydrates. In further embodiments, the C6 carbohydrates are selected from the group consisting of glucose, mannose, fructose, allose, gulose, idose, galactose, talose, sorbose, tagatose, and psicose. In some embodiments, one or more substrates are disaccharides. In further embodiments, the disaccharides are selected from the group consisting of sucrose, lactose, lactulose, maltose, trehalose, cellobiose, and chitobiose.

The processes of this disclosure are broadly applicable to any source of fermentable sugars such as from any suitable biomass source, including, but not limited to, one or more of corn, wheat, sugar beets, oats, barley, sugar cane, sorghum, cassava, rice, wood and the like and from cellulosic biomass. Lignocellulosic biomass is typically treated to recover cellulose and hemicellulose which can then be converted to sugars. Fermentable sugar may be derived or obtained from lignocellulose. The biomass is typically subjected to pretreatment which typically includes a physical and/or chemical pretreatment followed by an enzymatic and/or physical and/or chemical hydrolysis to convert cellulose, hemicellulose and/or starches to sugars. The fermentable sugar can be supplied to the bioreactor in any suitable form including, but not limited to, solid granules, slurries containing undissolved sugar solids, molasses and syrups. Where undissolved sugar solids are introduced into the bioreactor, sufficient water is present in the bioreactor to dissolve the sugars. It is not essential that all undissolved sugars introduced into the bioreactor become dissolved in the bioreactor, and the fermentation broth withdrawn from the bioreactor can contain undissolved sugar. The sugars may be fermentable or a combination of fermentable and non-fermentable sugars.

Process for Production of Desired Products

The present disclosure teaches that the process for production of desired products is performed in two phases or alternatively as a one-phase process. The two-phase process is constituted of a growth phase followed by a production phase. In the one-phase process growth and production phases take place at the same time. In some embodiments, the disclosure contemplates microbes, enzymatic pathways, genetic elements, and genetic modifications that may be utilized in the simultaneous production of MEG with one or more of ACE, IPA, and propene; as disclosed in U.S. Patent Application Publication US20170260551A1.

Two-Phase Process i. Growth (Propagation) Phase

The two-phase process is typically performed as described herewith. In the growth phase, recombinant microorganism such as E. coli is aerobically grown from a slant tube or a vial or any other known method of microorganism preservation using culture media (MM). The growth phase is performed in one or more stage flasks or bioreactors of appropriated culture media (MM) volumes, which increases over passages until reach the bioreactor, or a series of bioreactors achieving high cell density productivity.

In some embodiments, the set point of the dissolved oxygen concentration in the growth phase is adjusted to a range of about 5% to 50% of oxygen ($O_2$) saturation in fermentation broth, in order that the consumed feedstocks such as C5 and C6 carbohydrates and/or sugars are directed mainly toward cell mass production. In some embodiments, the dissolved oxygen concentration in the media is never below 10% of air saturation.

The culture conditions during the growth phase are the following.

In some embodiments, a pH range controlled with diluted $H_2SO_4$ and KOH, or NaOH or $NH_4OH$ aqueous solution or gaseous $NH_3$ is between 5.0 to 9.0, 5.5 to 8.0, 6.0 to 7.5, and 6.5 to 7.0. In some embodiments, a pH range controlled between 6.5 to 7.0 automatically with diluted $H_2SO_4$ and KOH or NaOH or $NH_4OH$ aqueous solution or gaseous $NH_3$.

The control of pH in a fermentation reaction is a critical factor that can affect a number of variables such as the reaction rate and product formed. Although the microorganisms involved in the fermentation will often produce products across a range of pH, maintaining an optimum pH for particular reaction conditions can maximize growth and/or production efficiency. The build-up of acids such as acetic acid and lactic acid can inhibit the fermentation and, if unchecked, can lead to collapse of the microorganism culture.

In broad terms, the disclosure also provides a method of controlling the pH of a fermentation broth in a bioreactor depending on bioreactor types for the pH of the broth to be continuously controlled.

In some embodiments, the controlled temperature is between 18-50° C., between 25-45° C., or between 32-40° C.; and. In some embodiments, the temperature controlled within the range of 32-40° C.

In further embodiments, total amount of C5 and/or C6 carbohydrates fed to the bioreactor during the growth phase is at least 5 kg carbohydrate/$m^3$, at least 10 kg carbohydrate/$m^3$, at least 20 kg carbohydrate/$m^3$, at least 30 kg carbohydrate/$m^3$, at least 40 kg carbohydrate/$m^3$, at least 50 kg carbohydrate/$m^3$, at least 60 kg carbohydrate/$m^3$, at least 70 kg carbohydrate/$m^3$, at least 80 kg carbohydrate/$m^3$, at least 90 kg carbohydrate/$m^3$, at least 100 kg carbohydrate/$m^3$, at least 150 kg carbohydrate/$m^3$, at least 200 kg carbohydrate/$m^3$, at least 250 kg carbohydrate/$m^3$, at least 300 kg carbohydrate/$m^3$, at least 400 kg carbohydrate/$m^3$ at least 500 kg carbohydrate/$m^3$, at least 600 kg carbohydrate/$m^3$, at least 700 kg carbohydrate/$m^3$, up to 800 kg carbohydrate/$m^3$. In some embodiments, total amount of C5 and/or C6 carbohydrates fed to the bioreactor during the growth phase ranges from about 10 kg carbohydrate/$m^3$ up to 500 kg carbohydrate/$m^3$.

The present disclosure teaches the culture media MM is balanced in terms of essential nutrients N, P, Mg and Fe among other elements to favor cell growth during the growth phase.

In some embodiments, the culture medium comprises Carbon (C) that is provided from C5 carbohydrates and/or C6 carbohydrates. In some embodiments, the culture medium comprises essential nutrients including Nitrogen (N), Phosphorus (P), Magnesium (Mg), and Iron (Fe). In some embodiments, the ratio of carbon (derived from C5 and C6 carbohydrates) to essential nutrients is as follows: C/N=1:1 to 20:1, C/P=5:1 to 30:1, C/Mg=30:1 to 400:1, C/Fe=30:1 to 400:1 in the growth phase.

The present disclosure also provides final cell mass concentration in the growth phase. In some embodiments, the final cell mass concentration in the growth phase is at least 1 kg/$m^3$, at least 2 kg/$m^3$, at least 3 kg/$m^3$, at least 4 kg/$m^3$, at least 5 kg/$m^3$, at least 10 kg/$m^3$, at least 20 kg/$m^3$, at least 30 kg/$m^3$, at least 40 kg/$m^3$, at least 50 kg/$m^3$, at least 60 kg/$m^3$, at least 70 kg/$m^3$, at least 80 kg/$m^3$, at least 90 kg/$m^3$, at least 100 kg/$m^3$, at least 110 kg/$m^3$, at least 120 kg/$m^3$, at least 130 kg/$m^3$, at least 140 kg/$m^3$, and at least 150 kg/$m^3$ of dried cell mass. In some embodiments, the final cell mass concentration in the growth phase ranges from 10 to 100 kg/$m^3$ of dry cell mass.

In some embodiments, time required for the growth phase varies between 1 to 200 hours. In further embodiments, the time of the growth phase is between 5 to 50 hours. The time is dependent on carbohydrate feeds and/or feedstocks.

ii. Production (Fermentation) Phase

For the production phase, cell mass of recombinant microorganism such as *E. coli* produced in the growth phase is transferred to another bioreactor. In some embodiments, the cell mass produced in the growth phase occupies at least about 1% to 50% of its working volume for production phase where the production of desired products are accomplished using culture media MM and carbohydrate feeds/feedstocks.

During the production phase, the culture conditions are limited (N, P) for *E. coli* growth and the consumed feedstocks such as C5 and C6 carbohydrates and/or sugars are deviated mainly to the production of MEG, ACE and IPA products.

In some embodiments, the total amount of C5 and/or C6 carbohydrates fed to the bioreactor during the production phase is at least 50 kg carbohydrate/$m^3$, at least 60 kg carbohydrate/$m^3$, at least 70 kg carbohydrate/$m^3$, at least 80 kg carbohydrate/$m^3$, at least 90 kg carbohydrate/$m^3$, at least 100 kg carbohydrate/$m^3$, at least 150 kg carbohydrate/$m^3$, at least 200 kg carbohydrate/$m^3$, at least 250 kg carbohydrate/$m^3$, at least 300 kg carbohydrate/$m^3$, at least 400 kg carbohydrate/$m^3$, at least 500 kg carbohydrate/$m^3$, at least 600 kg carbohydrate/$m^3$, at least 700 kg carbohydrate/$m^3$, at least 800 kg carbohydrate/$m^3$, at least 900 kg carbohydrate/$m^3$ up to 1000 kg carbohydrate/$m^3$. In some embodiments, total amount of C5 and/or C6 carbohydrates fed to the bioreactor during the production phase ranges from about 100 kg carbohydrate/$m^3$ up to 800 kg carbohydrate/$m^3$.

In some embodiments, time required for the production phase varies between 5 to 500 hours. In further embodiments, the time for the production phase varies from 10 to 300 hours for batch and fed-batch operations. In other embodiments, the time of the production phase is up to 300 hours with continuous fermentation.

In one embodiment of the disclosure, the dissolved oxygen concentration in the production phase is adjusted to a range between 0 to 10% of 02 saturation in fermentation broth in order to limit the *E. coli* growth and direct the carbon flux to primarily MEG, ACE and IPA production. However, at the beginning of the fermentation process the 02 saturation may be higher.

In another embodiment of the disclosure, the culture media MM in the production phase is adjusted to Carbon: Essential Nutrients ratios as following: C/N>10, C/P>20, C/Mg>200 and C/Fe>400, in order to limit the *E. coli* growth and deviate the carbon flux primarily to MEG, ACE and IPA production.

The present disclosure teaches the culture media MM is balanced in terms of essential nutrients N, P, Mg and Fe among other elements to favor production and cell maintenance during the production phase.

In some embodiments, the culture medium in the production phase comprises Carbon (C) that is provided from C5 carbohydrates and/or C6 carbohydrates. In some embodiments, the culture medium comprises essential nutrients including Nitrogen (N), Phosphorus (P), Magnesium (Mg), and Iron (Fe). In some embodiments, a ratio of C:N in the production phase is at least 10:1, at least 15:1, at least 20:1, at least 25:1, and at least 30:1. In other embodiments, a ratio of C:P in the production phase is at least 10:1, at least 15:1, at least 20:1, at least 30:1, at least 40:1, and at least 50:1. In other embodiments, a ratio of C:Mg in the production phase is at least 100:1, at least 200:1, at least 300:1, at least 400:1, and at least 500:1. In other embodiments, a ratio of C:Fe in the production phase is at least 300:1, at least 400:1, and at least 500:1. In other embodiments, the culture media MM in the production phase is adjusted to ratios of Carbon to Essential Nutrients as follows: C/N>10, C/P>20, C/Mg>200 and C/Fe>400 in the production phase.

One-Phase Process

The one-phase process is performed as described here. The growth and the production phases are simultaneously accomplished in the one-phase process. The recombinant microorganism such as *E. coli* is cultivated in a bioreactor using the culture media MM using the same pH and temperature conditions as described in the growth phase of the two-phase process.

The present disclosure teaches that microorganism cells are cultured for growth and propagation in such a way that a limitation in essential nutrients of culture media MM occurs. The present disclosure provides limitations in N, P, Mg or Fe, or alternatively limitation in dissolved oxygen concentration in the culture media. These limitations led to increases in the production rate of MEG, ACE and IPA, at the expense of the decrease of cell growth rate of microorganisms such as *E. coli*. The range of parameters used for the one-phase process production are the same as described for the production phase in the two-phase process production.

In some embodiments, the total amount of C5 and/or C6 carbohydrates fed to the bioreactor for one-phase process is at least 50 kg carbohydrate/m$^3$, at least 60 kg carbohydrate/m$^3$, at least 70 kg carbohydrate/m$^3$, at least 80 kg carbohydrate/m$^3$, at least 90 kg carbohydrate/m$^3$, at least 100 kg carbohydrate/m$^3$, at least 150 kg carbohydrate/m$^3$, at least 200 kg carbohydrate/m$^3$, at least 250 kg carbohydrate/m$^3$, at least 300 kg carbohydrate/m$^3$, at least 400 kg carbohydrate/m$^3$, at least 500 kg carbohydrate/m$^3$, at least 600 kg carbohydrate/m$^3$, at least 700 kg carbohydrate/m$^3$, at least 800 kg carbohydrate/m$^3$, at least 900 kg carbohydrate/m$^3$ up to 1000 kg carbohydrate/m$^3$. In some embodiments, total amount of C5 and/or C6 carbohydrates fed to the bioreactor during the production phase ranges from about 100 kg carbohydrate/m$^3$ up to 800 kg carbohydrate/m$^3$.

In some embodiments, time required for the production phase in the one-phase process varies between 5 to 500 hours. In further embodiments, the time required for production phase in the one-phase process varies between 5 to 300 hours.

In some embodiments, the one-phase or multi-phase production processes take about 5, about 10, about 25, about 50, about 75, about 100, about 125, about 150, about 175, about 200, about 225, about 250, about 275, about 300 about 325, about 350, about 375, about 400, about 425, about 450, about 475, or about 500 hours.

In some embodiments, the one-phase or multi-phase production processes take 5, 10, 25, 50, 75, 100, 125, 150, 175, 200, 225, 250, 275, 300 325, 350, 375, 400, 425, 450, 475, or 500 hours.

Desired End-Products

In some embodiments, MEG is produced simultaneously with one or more of ACE, IPA, and propene. In some embodiments, MEG is produced simultaneously with ACE. In some embodiments, MEG is produced simultaneously with IPA. In some embodiments, MEG is produced simultaneously with propene. In some embodiments, MEG is produced simultaneously with ACE and IPA. In some embodiments, MEG is produced simultaneously with ACE and propene. In some embodiments, MEG is produced simultaneously with IPA and propene. In some embodiments, MEG is produced simultaneously with ACE, IPA, and propene.

In some embodiments, at least one or more of MEG, ACE, IPA, and propene accumulations in the fermentation broth or anywhere in one or more of the bioreactors negatively impact the viability, growth, and/or production rates of the microorganisms. In some embodiments, maintaining a maximum concentration of one or more of MEG, IPA, ACE, or propene in the fermentation broth or in one or more of the bioreactors prevents negative impacts on viability, growth, and/or production rates of the microorganisms.

In some embodiments, one or more of MEG, IPA, ACE, and propene are continually removed from the bioreactor system to mitigate the negative impacts of the presence or high concentration of the molecules. In some embodiments, the molecules are continuously removed from the bioreactor system. In some embodiments, the molecules are remove in batches.

In some embodiments, the removal of the desired products is performed through off-gassing one or more of the bioreactors or one or more chambers of the bioreactor(s). In some embodiments, the off gassing is mixed with a solvent to dissolve the gas in the solute prior to recovery of the desired products. In some embodiments, the removal of the desired products is performed by drawing off on or more of the media, broth, or feedstock from one or more of the bioreactors or one or more changes of the bioreactor(s). In some embodiments, the cells are excluded from the media, broth, or feedstock prior to the removal of the desired products.

In some embodiments, the negative impacts include death of the microbes, decreased metabolic activity of the microbes, decreased production of one or more of MEG, IPA, ACE, or propone, inhibition of microbial growth and/or reproduction, inhibition of protein expression, and combinations thereof.

In some embodiments, MEG is produced at least 1 kg/m$^3$ h, at least 2 kg/m$^3$ h, at least 3 kg/m$^3$ h, at least 4 kg/m$^3$ h, at least 5 kg/m$^3$ h, 6 kg/m$^3$ h, at least 7 kg/m$^3$ h, at least 8 kg/m$^3$ h, at least 9 kg/m$^3$ h, at least 10 kg/m$^3$ h, at least 15 kg/m$^3$ h, at least 20 kg/m$^3$ h.

In some embodiments, ACE is produced at least 0.5 kg/m$^3$ h, at least 1 kg/m$^3$ h, at least 2 kg/m$^3$ h, at least 3 kg/m$^3$ h, at least 4 kg/m$^3$ h, at least 5 kg/m$^3$ h, 6 kg/m$^3$ h, at least 7 kg/m$^3$ h, at least 8 kg/m$^3$ h, at least 9 kg/m$^3$ h, at least 10 kg/m$^3$ h, at least 15 kg/m$^3$ h, at least 20 kg/m$^3$ h.

In some embodiments, IPA is produced at least at least 0.5 kg/m$^3$ h, 1 kg/m$^3$ h, at least 2 kg/m$^3$ h, at least 3 kg/m$^3$ h, at least 4 kg/m$^3$ h, at least 5 kg/m$^3$ h, 6 kg/m$^3$ h, at least 7 kg/m$^3$ h, at least 8 kg/m$^3$ h, at least 9 kg/m$^3$ h, at least 10 kg/m$^3$ h, at least 15 kg/m$^3$ h, at least 20 kg/m$^3$ h.

In some embodiments, propene is produced at least at least 0.5 kg/m$^3$ h, 1 kg/m$^3$ h, at least 2 kg/m$^3$ h, at least 3 kg/m$^3$ h, at least 4 kg/m$^3$ h, at least 5 kg/m$^3$ h, 6 kg/m$^3$ h, at least 7 kg/m$^3$ h, at least 8 kg/m$^3$ h, at least 9 kg/m$^3$ h, at least 10 kg/m$^3$ h, at least 15 kg/m$^3$ h, at least 20 kg/m$^3$ h.

In some embodiments, the combined products of the biological processes of the present disclosure result in a production of at least 1 kg/m$^3$ h, at least 2 kg/m$^3$ h, at least 3 kg/m$^3$ h, at least 4 kg/m$^3$ h, at least 5 kg/m$^3$ h, 6 kg/m$^3$ h, at least 7 kg/m$^3$ h, at least 8 kg/m$^3$ h, at least 9 kg/m$^3$ h, at least 10 kg/m$^3$ h, at least 15 kg/m$^3$ h, or at least 20 kg/m$^3$ h of MEG, acetone, isopropanol propene, precursors thereof, and/or mixtures thereof.

Figure 2:
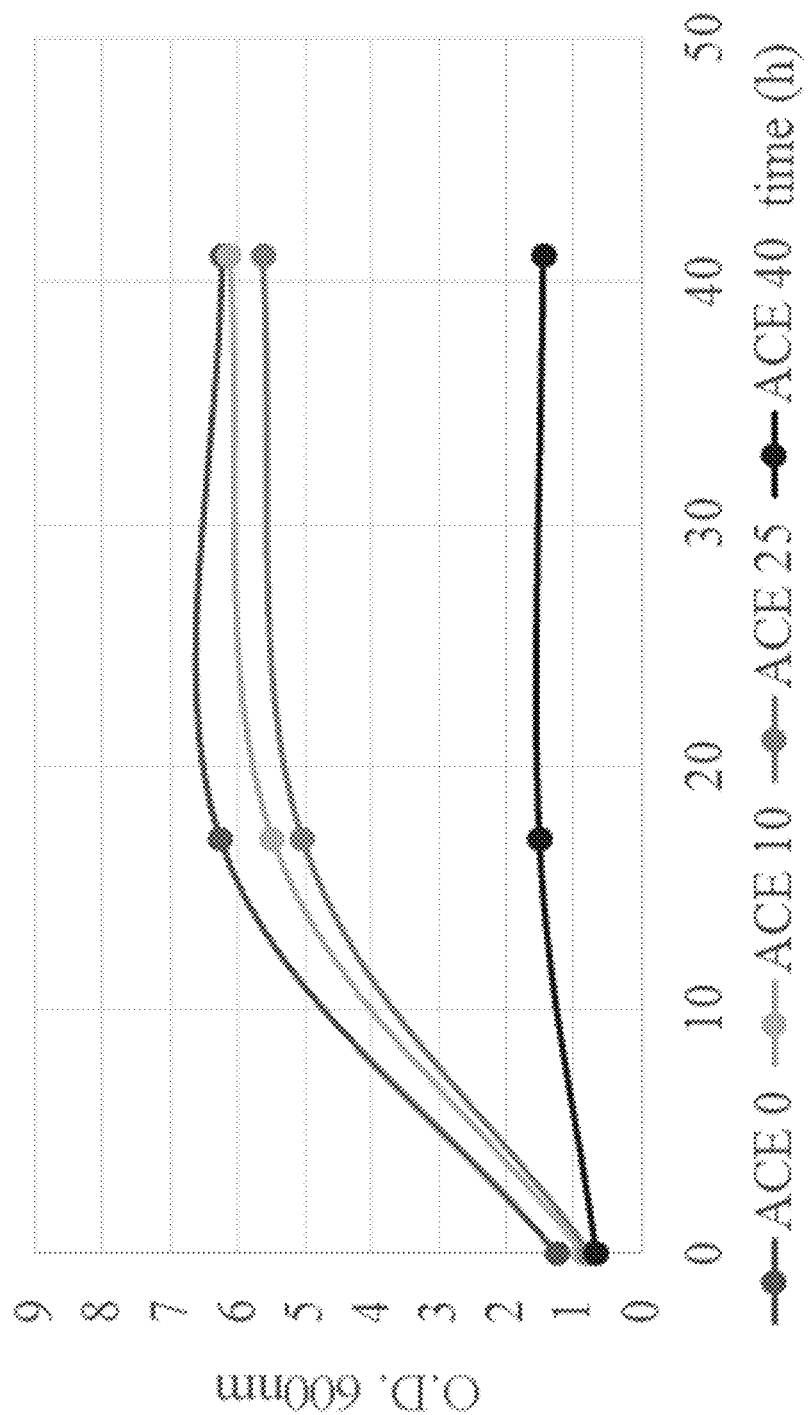
FIG. 2 illustrates the tolerance of *E. coli* grown in culture media with increasing values of acetone (ACE).

FIGS. 1 and 2 illustrate a growth rate decrease for increasing values of MEG, IPA and ACE. During the process production, the in situ fermentation broth removal of ACE and IPA, with or without concomitant in situ removal of MEG took place, thereby alleviating its inhibitory effects and increasing product concentration and product rate overall of MEG, ACE and IPA.

i. Monoethylene Glycol (MEG)

Monoethylene glycol (MEG) is an important raw material for industrial applications. A primary use of MEG is in the manufacture of polyethylene terephthalate (PET) resins, films and fibers. In addition, MEG is important in the production of antifreezes, coolants, aircraft anti-icer and deicers and solvents. MEG is also known as ethane-1,2-diol.

Ethylene glycol is also used as a medium for convective heat transfer in, for example, automobiles and liquid cooled computers.

Because of its high boiling point and affinity for water, ethylene glycol is a useful desiccant. Ethylene glycol is widely used to inhibit the formation of natural gas clathrates (hydrates) in long multiphase pipelines that convey natural gas from remote gas fields to a gas processing facility. Ethylene glycol can be recovered from the natural gas and reused as an inhibitor after purification treatment that removes water and inorganic salts.

Minor uses of ethylene glycol include in the manufacture of capacitors, as a chemical intermediate in the manufacture of 1,4-dioxane, and as an additive to prevent corrosion in liquid cooling systems for personal computers. Ethylene glycol is also used in the manufacture of some vaccines; as a minor ingredient in shoe polish, inks and dyes; as a rot and fungal treatment for wood; and as a preservative for biological specimens.

ii. Acetone

Acetone (also known as propanone) is an organic compound with the formula $(CH_3)_2CO$. It is a colorless, volatile, flammable liquid, and is the simplest of the ketones.

Acetone is miscible with water and serves as an important solvent, typically for cleaning purposes in the laboratory. Over 6.7 million tonnes are produced worldwide, mainly for use as a solvent and production of methyl methacrylate and bisphenol A. It is a common building block in organic chemistry. Familiar household uses of acetone are as the active ingredient in nail polish remover and as paint thinner.

iii. Isopropanol

Isopropyl alcohol (IUPAC name 2-propanol), also called isopropanol, is a compound with the chemical formula $C_3H_8O$ or $C_3H_7OH$ or $CH_3CHOHCH_3$. It is a colorless, flammable chemical compound with a strong odor. It is the simplest example of a secondary alcohol, where the alcohol carbon atom is attached to two other carbon atoms sometimes shown as $(CH_3)_2CHOH$. It is a structural isomer of propanol. It has a wide variety of industrial and household uses.

The first and biggest use of isopropanol (IPA) is as a solvent. The other most significant use of IPA is as a chemical intermediate. It is a component of cleaners, disinfectants, room sprays, lacquers and thinners, adhesives, pharmaceuticals, cosmetics and toiletries. It is also used as an extractant and as a dehydrating agent. Xanthan gum, for example, is extracted with IPA. In addition, isopropanol is also used as a gasoline additive, to dissolve water and ice in fuel lines and tanks thereby preventing the water from accumulating in the fuel lines and freezing at low temperatures. IPA is also sold as rubbing alcohol and used as a disinfectant.

iv. Propene

Propene, also known as propylene or methyl ethylene, is an unsaturated organic compound having the chemical formula $C_3H_6$. It has one double bond, and is the second simplest member of the alkene class of hydrocarbons.

Propene is produced from fossil fuels-petroleum, natural gas, and, to a much lesser extent, coal. Propene is a byproduct of oil refining and natural gas processing.

Propene is the second most important starting product in the petrochemical industry after ethylene. It is the raw material for a wide variety of products such as bumpers for cars, food containers, films, medical instruments, and the like. Manufacturers of the plastic polypropylene account for nearly two thirds of all demand. Polypropylene is, for example, needed for the production of films, packaging, caps and closures as well as for other applications. Propene is also used for the production of important chemicals such as propylene oxide, acrylonitrile, cumene, butyraldehyde, and acrylic acid. Over 85 million tonnes of propene is processed worldwide.

Fermentation

The present disclosure is generally drawn to the use of carbohydrate substrates derived from biomass. In some embodiments, the carbohydrate substrates include C5 and C6 molecules. In some embodiments, recombinant microorganisms are utilized to produce MEG and one or more C3 compounds, particularly acetone, isopropanol, and propene within one or more bioreactors. Those skilled in the art will be aware upon consideration of the instant disclosure that the methods and/or processes described herein may be applied to other fermentation reactions including those using the same or different microorganisms Thus, the scope of the present disclosure is not limited to the particular embodiments and/or applications described, rather it to be understood in a broader sense; for example, the source of the substrates and feedstocks described herein is not limiting, other than that at least a component thereof is useful to feed a fermentation reaction.

However, microorganisms used for processes for the production of ethanol and other alcohols from gaseous substrates are well known to those of ordinary skill in the art. It should be understood that aerobes and/or anaerobes may be utilized for modifying or optimizing useful to produce C3 compounds described herein. The methods and processes are not limited to just one type of microorganism, rather one or more microorganisms may be utilized at the same time in co-culture or in different phases or components of the bioreactor(s). Exemplary processes include those described for example in WO2007/117157. WO02008115080, WO2009/022925, WO2009/064200, U.S. Pat. Nos. 6,340, 581, 6,136,577, 5,593,886, 5,807,722 and 5,821,111, each of which is incorporated herein by reference. A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al. Biotechnology Letters 29: pp 1607-1612), and those of the genus *Carboxydothermus* (Svetlichny. V. A., Sokolova, T. G. et al (1991). Systematic and Applied Microbiology 14: 254-260). Further examples include *Moorella thermoacetica, Moorella thermoautotrophica, Rumincocclus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65).

In one embodiment, a microorganism suitable for use in the present disclosure is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the

*Clostridium autoethanogenum* is a *Clostridium autoethanogenum* having the identifying characteristics of DSMZ deposit number DSMZ 10061.

In some embodiments, microorganism for use in the methods of the present disclosure can be selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula, Myxozyma, Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some embodiments, microorganisms for use in the methods of the present disclosure include *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp, *Corynebacterium* sp., *Yarrowia lipolytica, Scheffersomyces stipitis,* and *Terrisporobacter glycolicus.*

Culturing of the microorganisms used in the methods of the disclosure may be conducted using any number of processes known in the art for culturing and fermenting substrates using the microorganisms. Exemplary techniques are provided in the "Examples" section below. By way of further example, those processes generally described in the following articles using gaseous substrates for fermentation may be utilized: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel, 70. 605-614; (iii) K. T Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling 3, 149-160; all of which are incorporated herein by reference.

The fermentation may be carried out in any suitable bioreactor, such as Continuous Stirred Tank Bioreactor, Bubble Column Bioreactor. Airlift Bioreactor. Fluidized Bed Bioreactor, Packed Bed Bioreactor. Photo-Bioreactor, Immobilized Cell Reactor. Trickle Bed Reactor, Moving Bed Biofilm Reactor, Bubble Column, Gas Lift Fermenter. Membrane Reactors such as Hollow Fiber Membrane Bioreactor. Also, in some embodiments, the bioreactor comprises a first, growth reactor in which the microorganisms are cultured, and a second, fermentation reactor, to which fermentation broth from the growth reactor is fed and in which most of the fermentation product (e.g. MEG, acetone, isopropanol, and propene) is produced. In some embodiments, the bioreactor simultaneously accomplishes the culturing of microorganism and the producing the fermentation product (e.g. MEG, acetone, isopropanol, and propene) from carbon sources such substrates and/or feedstocks provided.

According to various embodiments, the carbon source for the fermentation reaction is C5 carbohydrates (pentose) and/or C6 carbohydrates (hexose). The substrate for the fermentation reaction is C5 and/C6 sugars, their derivatives from biomass including but not limited to corn starch, sugarcane juice, crop residues such as corn stover and sugarcane bagasse, purpose-grown grass crops, and woody plants. For example, biomass by-products are obtained during the extraction and processing of foodstuffs such as sugar from sugarcane, or starch from maize or grains, or non-food biomass waste generated by the forestry industry.

The present disclosure teaches growth of the recombinant microorganisms and fermentation to occur, in addition to the substrate feedstocks, with a suitable liquid culture medium and/or nutrient medium that need to be fed to the bioreactor. A culture medium contains vitamins and minerals sufficient to permit growth of the microorganism used. For example, suitable media for growth of anaerobic media suitable for the fermentation of ethanol using CO as the sole carbon source are described in U.S. Pat. Nos. 5,173,429 and 5,593,886 and WO 02/08438, WO2007/115157 and WO2008/115080. The present disclosure pros ides a culture media which has increased efficacy in supporting growth of the microorganisms for production of MEG and one or more C3 compounds in the fermentation process.

In some embodiments, one or more gaseous substrates are provided to the bioreactor. The gaseous substrates include molecular hydrogen, carbon dioxide, carbon monoxide, and syngas.

In some embodiments, upon carbohydrate depletion or near-carbohydrate depletion of the media, a carbon source pulse is performed.

The fermentation should desirably be carried out under appropriate conditions for the desired fermentation to occur. Reaction conditions that should be considered include pressure, temperature, gas flow rate, liquid flow rate, media pH, media redox potential, agitation rate (if using a continuous stirred tank reactor), inoculum level, maximum substrate concentrations to ensure that substrates/feedstocks in the production phase does not become limiting, and maximum product concentrations to avoid product inhibition. Suitable conditions are described in WO02/08438, WO07/117,157 and WO08/115,080.

Desired end product production rate, which is a key determinant as to whether a given fermentation process is economically attractive, is highly dependent on managing the appropriate conditions for microorganism growth. For example, it is known from WO2010/093262 that the CO-containing substrate must be provided to a microbial culture at a rate that results in optimal microbial growth and/or desired metabolite production. If insufficient substrate is provided, microbial growth slows and the fermentation product yields shift toward acetic acid at the expense of ethanol. If excessive substrate is provided, poor microbial growth and/or cell death can result. Further information regarding the relationships among operating parameters in these processes is found in WO2011/002318.

The control of operating parameters is particularly important during the initial period of operation, in which the processing objectives are focused on not only growing the cell culture to a sufficient level and establishing other conditions for continuous operation, but also balancing the product and byproduct productivities. Reducing the time needed for conducting a batch culture operation, prior to continuous bioreactor operation, has major implications for improving process economics. This is particularly true in view of the fact that microbes capable of growing on sugars as a food source generally do so at a faster rate than microbes used in competing technologies with CO-containing gases. From the commercial perspective of operating a fermentation process, the time required for a microbial population to become established, i.e., to reach a sufficiently high cell density for the synthesis of economically favorable levels of product, represents a key operating cost affecting the overall profitability. The ability to enhance culture growth rates and/or productivities during an initial operating period, for example under batch conditions, and thereby reduce the time required to reach desired cell densities and/or product levels, is an important determinant for overall success in the commercialization of biological processes for producing MEG and one or more C3 compounds from C5 and C6 sugars from biomass.

Product Recovery

The products generated in the disclosed methods can be recovered using a variety of techniques. Exemplary methods include those described m WO07/117,157, WO08/115,080, U.S. Pat. Nos. 6,340,581, 6,136,577, 5,593,886, 5,807,722 and 5,821,111. However, briefly and by way of example alcohols may be recovered from the fermentation broth by methods such as fractional distillation or evaporation, extractive fermentation, and pervaporation.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is nonvolatile and is recovered for re-use in the fermentation.

Acetate, which is produced as a by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate.

Other methods for recovering acetate from a fermentation broth are also known in the art. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth m either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system. In some embodiments, pervaporation is used to separate products from a mixture.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

In some embodiments, removal of the volatile products is performed by gas stripping, which includes aerating the composition in which the products are being produced at a rate appropriate to supply oxygen and to strip the volatile products from the composition to a bioreactor off gas chamber. In some embodiments, a water trap is utilized to collect the volatile products from the gas by bubbling the gas through volumes of water or other solvent.

Bioreactors

Bioreactors can be divided into two broad categories, batch reactors and continuous reactors. Batch reactors are generally stirred tanks sufficiently large to handle the full inventory of a complete batch cycle. In some cases, batch reactors may be operated in semi-batch mode where one chemical is charged to the vessel and a second chemical is added slowly. Continuous reactors are generally smaller than batch reactors and handle the product as a flowing stream. Continuous reactors may be designed as pipes with or without baffles or a series of interconnected stages or phases. The advantages of batch reactors are as follows: 1) batch reactors are very versatile and are used for a variety for different unit operations (batch distillation, storage, crystallization, liquid-liquid extraction etc.) in addition to chemical reactions; 2) there is a large installed base of batch reactors within industry and their method of use is well established; 3) batch reactors are excellent at handling difficult materials like slurries or products with a tendency to foul; and 4) Batch reactors represent an effective and economic solution for many types of slow reactions.

On the other hand, benefits of continuous reactors are 1) the rate of many chemical reactions is dependent on reactant concentrations. Continuous reactors are generally able to cope with much higher reactant concentrations due to their superior heat transfer capacities. Plug flow reactors have the additional advantage of greater separation between reactants and products giving a better concentration profile; 2) the small size of continuous reactors makes higher mixing rates possible; and 3) the output from a continuous reactor can be altered by varying the run time. This increases operating flexibility for manufacturers.

Bioreactors can be Further Divided into 6 Subtypes.

i. Continuous Stirred Tank Bioreactors

A continuous stirred tank bioreactor consists of a cylindrical vessel with motor driven central shaft that supports one or more agitators (impellers). The shaft is fitted at the bottom of the bioreactor. The number of impellers is variable and depends on the size of the bioreactor i.e., height to diameter ratio, referred to as aspect ratio. The aspect ratio of a stirred tank bioreactor is usually between 3-5. However, for animal cell culture applications, the aspect ratio is less than 2. The diameter of the impeller is usually ⅓ rd of the vessel diameter. The distance between two impellers is approximately 1.2 impeller diameter. Different types of impellers (Rustom disc, concave bladed, marine propeller etc.) are in use. In stirred tank bioreactors or in short stirred tank reactors (STRs), the air is added to the culture medium under pressure through a device called sparger. The sparger may be a ring with many holes or a tube with a single orifice. The sparger along with impellers (agitators) enables better gas distribution system throughout the vessel. The bubbles generated by sparger are broken down to smaller ones by impellers and dispersed throughout the medium. This enables the creation of a uniform and homogeneous environment throughout the bioreactor. There are many advantages of STRs over other types. These include the efficient gas transfer to growing cells, good mixing of the contents and flexible operating conditions, besides the commercial availability of the bioreactors.

ii. Bubble Column Bioreactors

In the bubble column bioreactor, the air or gas is introduced at the base of the column through perforated pipes or plates, or metal micro porous spargers. The flow rate of the air/gas influences the performance factors—$O_2$ transfer, mixing. The bubble column bioreactors may be fitted with perforated plates to improve performance. The vessel used for bubble column bioreactors is usually cylindrical with an aspect ratio of 4-6 (i.e., height to diameter ratio).

iii. Airlift Bioreactors

In the airlift bioreactors, the medium of the vessel is divided into two interconnected zones by means of a baffle or draft tube. In one of the two zones referred to a riser, the air/gas is pumped. The other zone that receives no gas is the down comer. The dispersion flows up the riser zone while the down flow occurs in the down comer. There are two types of airlift bioreactors. 1) Internal-loop airlift bioreactor has a single container with a central draft tube that creates interior liquid circulation channels. These bioreactors are simple in design, with volume and circulation at a fixed rate for fermentation. 2) External loop airlift bioreactor possesses an external loop so that the liquid circulates through separate independent channels. These reactors can be suitably modified to suit the requirements of different fermentations. In general, the airlift bioreactors are more efficient than bubble columns, particularly for more dense suspensions of microorganisms. This is mainly because in these bioreactors, the mixing of the contents is better compared to bubble columns.

Airlift bioreactors are commonly employed for aerobic bioprocessing technology. They ensure a controlled liquid flow in a recycle system by pumping. Due to high efficiency, airlift bioreactors are sometimes preferred e.g., methanol production, waste water treatment, single-cell protein production. In general, the performance of the airlift bioreactors is dependent on the pumping (injection) of air and the liquid circulation.

Two-stage airlift bioreactors are used for the temperature dependent formation of products. Growing cells from one bioreactor (in one instance, maintained at temperature 30° C.) are pumped into another bioreactor (in one instance, at temperature 42° C.). There is a necessity for the two-stage airlift bioreactor, since it is very difficult to raise the temperature quickly from 30° C. to 42° C. in the same vessel. Each one of the bioreactors is fitted with valves and they are connected by a transfer tube and pump. The cells are grown in the first bioreactor and the bioprocess proper takes place in the second reactor.

A pressure-cycle fermenter with large dimensions constitutes a tower bioreactor. A high hydrostatic pressure generated at the bottom of the reactor increases the solubility of $O_2$ in the medium. At the top of the riser, (with expanded top) reduces pressure and facilitates expulsion of $CO_2$. The medium flows back in the down comer and completes the cycle. The advantage with tower bioreactor is that it has high aeration capacities without having moving parts.

iv. Fluidized Bed Bioreactors

Fluidized bed bioreactor is comparable to bubble column bioreactor except the top position is expanded to reduce the velocity of the fluid. The design of the fluidized bioreactors (expanded top and narrow reaction column) is such that the solids are retained in the reactor while the liquid flows out. These bioreactors are suitable for use to carry out reactions involving fluid suspended biocatalysts such as immobilized enzymes, immobilized cells, and microbial flocs.

For an efficient operation of fluidized beds, gas is spared to create a suitable gas-liquid-solid fluid bed. It is also necessary to ensure that the suspended solid particles are not too light or too dense (too light ones may float whereas to dense ones may settle at the bottom), and they are in a good suspended state. Recycling of the liquid is important to maintain continuous contact between the reaction contents and biocatalysts. This enable good efficiency of bioprocessing.

v. Packed Bed Bioreactors

A bed of solid particles, with biocatalysts on or within the matrix of solids, packed in a column constitutes a packed bed bioreactor. The solids used may be porous or non-porous gels, and they may be compressible or rigid in nature. A nutrient broth flows continuously over the immobilized biocatalyst. The products obtained in the packed bed bioreactor are released into the fluid and removed. While the flow of the fluid can be upward or downward, down flow under gravity is preferred.

The concentration of the nutrients (and therefore the products formed) can be increased by increasing the flow rate of the nutrient broth. Because of poor mixing, it is rather difficult to control the pH of packed bed bioreactors by the addition of acid or alkali. However, these bioreactors are preferred for bioprocessing technology involving product-inhibited reactions. The packed bed bioreactors do not allow accumulation of the products to any significant extent.

Furthermore, bioreactors having a selectively permeable porous material with an open pore structure are well known to those of ordinary skill in the art. See, for example, U.S. Patent Application Publication No. US20090130704, which is expressly incorporated herein by reference in its entirety. Bioreactors can be categorized into five classes by methods utilized for gas exchange, presence, or absence of means for photoradiation delivery, and ability to maintain monoseptic conditions.

Class I bioreactors have organisms or cells contained and isolated physically from the outside environment to maintain monoseptic conditions within the bioreactor. Gases are forcibly introduced and/or injected as a distinct phase into the culture fluid. Gases include those used for respiration, aerobic metabolism as well as inert gases used to promote anaerobic conditions and sweep gaseous and volatile products and by-products out of the reactor. Universally, in this class of reactors, product and by-product gases exit the reactor via a means separate and independent from the point of forced introduction. The culture fluid is forcibly agitated (i.e., hydraulic movement by means other than natural convection) either by a separate stirrer or by the forced introduction of gases as a distinct phase into the culture fluid. Examples include conventional stirred tank and airlift bioreactors for the production of chemicals, pharmaceuticals, and small molecules.

Class II bioreactors have organisms or cells contained and isolated physically from the outside environment to maintain monoseptic conditions within the bioreactor. Gases are passively introduced to the culture fluid, but NOT as a distinct phase. Means of introduction or transfer can be by migration through a gas-permeable material that separates the bulk gas phase from the bulk liquid phase and also serves to isolate the culture fluid physically from the outside environment. Gases include those used for respiration, aerobic metabolism as well as inert gases used to promote anaerobic or other special conditions within the reactor. Product and/or by-product gases exit the bioreactor via a separate vent as a distinct phase or via migration through the same or another section of a gas permeable material that also serves to isolate the culture fluid physically from the outside environment. The culture fluid may or may not be forcibly agitated. Examples include small and large cell culture reactors and microbial reactors for the production of chemicals, pharmaceuticals, or gases.

Class III bioreactors are identical to Class I bioreactors except that the culture fluid is illuminated or photoradiated to provide electromagnetic radiation as an integral raw material or component of the process. Variations are known in the art for maximizing light delivery to the organisms (e.g., Gordon (2002) Intl J of Hydrogen Energy 27:1175-1184). Examples include conventional bioreactors that are also illuminated either internally or externally for the production of chemicals, pharmaceuticals, or small molecules. Examples include bioreactors whose purpose includes deactivation of all organisms or cells by exposure to electromagnetic radiation.

Class IV bioreactors are identical to Class II bioreactors except that the culture fluid is illuminated or photoradiated to provide electromagnetic radiation as an integral raw material or component of the process. Examples include small and large cell culture reactors and microbial reactors for the production of chemicals, pharmaceuticals, or gases. Examples include bioreactors whose purpose includes deactivation of all organisms or cells by exposure to electromagnetic radiation.

Class V bioreactors have organisms or cells that are not isolated physically from the outside environment. Monoseptic conditions are not maintained within the bioreactor. Gases are passively introduced to the culture fluid by mass transfer from a bulk gas phase present above and in contact with the surface of the culture fluid. Mass transfer occurs passively at the gas liquid interface. Mass transfer is passive because the bulk gas phase is not pumped or injected. Gases include those used for respiration, aerobic metabolism as well as inert gases used to promote anaerobic or other special conditions within the culture fluid. Product and/or by-product gases leave the culture fluid via the same gas-liquid interfacial area. The culture fluid may or may not be forcibly agitated. The culture fluid may or may not be photoradiated. Examples include open ponds for cultivation of photosynthetic algal biomass (can be used as a dietary supplement) or for the production of chemicals using photosynthetic algae and/or photosynthetic bacteria as well as aerobic bacteria. Examples also include aerobic digestion of soluble organic matter by mixed bacterial cultures in a wastewater treatment plant. In Class V bioreactors selectively porous materials function as a barrier to minimize contamination of the culture fluid with foreign debris, while permitting photoradiation and gas exchange, if necessary.

Additional classes of bioreactors exist having different combinations of methods for gas exchange, presence or absence of means for photoradiation delivery, and ability to maintain monoseptic conditions.

Bioreactor designs, instructions for constructing bioreactors, and methods for using bioreactors can be found in: *Bioreactor Design Fundamentals* by Norton G. McDuffie, October '91, 137 pp. Pub: Butterworth-Heinemann. ISBN 0750691077; *Bioreactor System Design* by Juan A. Asenjo and J. C. Merchuk, January '95, 648 pp. Pub: Mercel Dekker. ISBN 0824790022; *Bioreactors in Biotechnology* by A. H. Scragg, September. '91, 300 pp, Pub: Prentice Hall Professional Technical References. ISBN 0130851434; *Cell Culture Systems and Conventional Bioreactor Technology* by H. Michelle Jones, November '97, 141 pp. Pub: Business Communications. ISBN 1569653828; *Growth and Synthesis: Fermenters, Bioreactors and Biomolecular Synthesizers* by William L. Hochfeld, October '94, 266 pp. Pub: CRC Press. ISBN 0935184627; *Membrane Bioreactors: Feasibility and Use in Water Reclamation* by Samer Adham and R. Shane Trussell, January '01, Pub: Water Environment Research Foundation. ISBN 1893664368; *Operational Models of Bioreactors* by Biotol Partners Staff, July '92, 282 pp. Pub: Butterworth-Heinemann. ISBN 0750615087; $3^{rd}$ *International Conference on Bioreactor and Bioprocess Fluid Dynamics* by American Society of Mechanical Engineers Staff, 568 pp. Pub: Professional Engineering Publishing; *Advances in Biochemical Engineering—Biotechnology: Bioreactor Systems and Effects* by A. Fiechter (ed.), October '91, 156 pp. Pub: Springer-Verlag New York, Inc. ISBN 0387540946; *Fermentation & Bioreactors*, August '87, Pub: Business Communications. ISBN 0893364045; *Bioreaction Engineering Principles* by Jens H. Nielsen, July '94, 480 pp. Pub: Kluwer Academic Publications ISBN 030644688X; *Airlift Bioreactors* by M. Y. Chisti. January '89, 350 pp. Pub Elsevier Science ISBN 1851663207; *Animal Cell Bioreactors* by Chester S. Ho (ed.) and Daniel I. Wang (ed.), January '91, 512 pp. Pub: Butterworth-Heinemann ISBN 0409901237; *Basic Bioreactor Design* by Klaas Van Riet and J. Tramper, January '91, 480 pp. Pub: Marcel Dekker ISBN 0824784464; *Bioreactor Design and Product Yield* by Biotol Board Staff, August '92, 275 pp. Pub: Butterworth-Heinemann ISBN 0750615095; *On-line Estimation and Adaptive Control of Bioreactors* by G. Bastin and D. Dochain (ed.), January '90 ISBN 0444884300; *Bioreaction Engineering, Vol. 2 Characteristic Features of Bioreactors* by K. Schugerl, May '91, 418 pp. Pub: John Wiley & Sons ISBN 0471925934; *Membrane Systems Analysis and Design: Applications in Biotechnology, Biomedicine and Polymer Science* by W. R Vieth, December '88, 360 pp. Pub:

John Wiley & Sons; *BioCatalytic Membrane Reactors* by Enrico Drioli and Lidietta Giomo, February '99, 211 pp. Pub: Taylor & Francis, Inc. ISBN 0748406549; *Biological Reaction Engineering: Principles, Applications and Modeling with PC Simulation* by I. J. Dunn, J. Ingham, E. Heinzle and J. E. Prenosil, November '92, 438 pp. Pub: John Wiley & Sons ISBN 3527285113; *Multiphase Bioreactor Design* by Joaquim M. Cabral (ed.), J. Tramper (ed.) and Manuel Mota (ed.), December '01, 528 pp. Pub: Taylor & Francis, Inc. ISBN 0415272092; and *Bioreaction Engineering: Modeling and Control* by K. Schugerl and Karl-Heinz Bellgardt (ed.), January '00, 600 pp, Pub: Springer-Verlag New York. Inc. ISBN 354066906X. Class I, II, III, and IV bioreactors can be batch, semi-batch or continuous systems and the geometry of any of the Classes I through IV can be a cylindrical vessel, a box shape, a tubular shape, etc. The open pond (Class V) style occurs in a variety of configurations. One example, called a racetrack design has a circulation means (e.g., a paddle slowly circulates the culture fluid) around a very long and narrow donut shaped bathtub that is open to the atmosphere. Other designs include a simple stagnant pond and an agitated bathtub where there is no pathwise movement of the culture fluid.

All known bioreactor types and methods for using bioreactors known in the art are useful in the practice of this invention, including, but not limited to, bioreactors and methods described in U.S. Pat. No. 5,763,279 (issued Jun. 9, 1998), U.S. Pat. No. 6,228,607 (issued May 8, 2001), U.S. Pat. No. 6,432,698 (issued Aug. 13, 2002), UK Patent application GB 2118572, Gordon (2002) Intl J of Hydrogen Energy 27:1175-1184, BioHydrogen (1998) Plenum Press, NY, Ed Zaborsky, WO 0231101 (filed on Oct. 10, 2001), EP 0 100 660 (filed on Jul. 29, 1983), JP 6000494 (published Jan. 11, 1994), Liang et al. (2002) Intl J of Hydrogen Energy 27:1157-165, OptiCell™. BioCrystal Ltd., Westerville, Ohio, WO 89/11529 (filed May 19, 1989), U.S. Pat. No. 6,492,149 (issued Dec. 10, 2002), EP 0 391 590 (filed on Mar. 27, 1990), Bioreactor system design/edited by Juan A. Asenjo, Jose C. Merchuk, Publisher New York: M. Dekker, c1995, van't Riet, Klaas Basic bioreactor design/Klaas van't Riet. Johannes Tramper Publisher New York: M. Dekker, c1991, and McDuffie, Norton G Bioreactor design fundamentals/Norton G. McDuffie Publisher Boston: Butterworth-Heinemann, c1991.

In some embodiments, bioreactor used in the process taught in this disclosure may be one selected from Continuous Stirred Tank Bioreactor, Bubble Column Bioreactor, Airlift Bioreactor, Fluidized Bed Bioreactor, and Packed Bed Bioreactors, to accomplish either, the growth and or the production phases. In some embodiments, the bioreactor types can be mixed and matched in multiple stages depending upon the production requirements desired.

Bioreactor Mode of Operation

The fermentation within the present disclosure proceeds in the presence of cells in either a batch system or an immobilized cell system. Suitable batch systems in this regard include a single-stage batch system, a fed-batch system, a continuous-fermenter train system and a multistage continuous batch system.

A single-stage batch system involves a one-step process in which the biocatalysts and/or microorganisms producing biocatalysts are added to a fermentable mixture in a fermentation vessel and allowed to ferment, after which the desired end products taught in the disclosure is separated from the fermentable mixture, and the biocatalysts and/or microorganisms producing biocatalysts are discarded. In a fed-batch system, a feeding stream is continuously added to the vessel until it reaches it's working volume. An aliquot of the fermentative mixture in a fermentation vessel can or cannot be removed at intervals during the fermentation process and be replaced by fresh fermentative mixture and nutrients, with or without the additional biocatalysts, also called fill-and-draw system. Fermentation in a continuous-fermenter train system involves continuous addition of fresh fermentable mixture and nutrients, with or without additional biocatalysts, to a fermentation vessel, which is serially connected to other vessels, such that overflow from the first vessel flows into the second vessel, and so forth. In an immobilized cell system, the biocatalysts are entrapped, e.g., in calcium or aluminum alginate gel particles.

In each of these systems, the cells used in the fermentation process can be recycled by centrifugation, filtration, flocculation, or coprecipitation with inert materials. For example, the recycled cells can be added to the fermentation mixture at different points in the multi-stage batch system.

In some embodiments, the processes and system for production described herein can be operated in the batch, fed-batch, fill-and-draw or continuous mode, which can provide the control of the flux of components of the culture media MM and in consequence increasing product yields and productivity. In some embodiments, at the end of the batch operation, fed-batch operation, or present at the outlet of continuous process, the produced cell mass can be separated from fermentation broth and used as inoculum for the next batch or fed-batch run, or be recycled to the bioreactor of the continuous process, increasing therefore the product formation rate and minimizing the need for consumption of carbohydrates for new cell growth.

EXAMPLES

Example 1: Co-Tolerance of *E. coli* to Monoethylene Glycol (MEG) and Acetone

Culture media composed of 10 g/L tryptone, 5 g/L yeast extract, 5 g/L NaCl, 9.4 g/L $K_2HPO_4$, 2.2 g/L $KH_2PO_4$, 7 g/L of xylose and different mixtures of synthetic Acetone and MEG was used to evaluate the co-tolerance to these products. A wild-type K12 strain of *E. coli* was grown in a 15 mL tube containing no MEG or acetone overnight at 37° C. and 200 rpm. This grown culture was used to inoculate a microplate containing the media with different concentrations of MEG+Acetone. The plate was incubated for 40 hours at 37° C. and 200 rpm. FIG. 1 illustrates the *E. coli* growth curve for increasing initial values of MEG+Acetone. For concentrations of Acetone up to 12 g/L and MEG up to 61 g/L no effect was observed on the growth profile of *E. coli*. At 15 g/L of Acetone and 79 g/L of MEG the growth is about half of the control strain. Increasing the concentration of MEG to 96 g/L has no impact on the result, showing that acetone concentration seems to be more critical to growth. 19 g/L of Acetone and 79 g/L of MEG seems to be the highest concentration of MEG+Acetone that allows growth, reaching an OD of about half the control strain. Higher concentrations of acetone completely impair growth, while higher concentrations of MEG (96 g/L) with lower concentration of acetone don't affect growth. This results show that the concentration of acetone in the broth will be critical for the production strain.

Example 2: *E. coli* Tolerance to Acetone

Culture media composed of 10 g/L tryptone, 5 g/L yeast extract, 5 g/L NaCl, 9.4 g/L $K_2HPO_4$, 2.2 g/L $KH_2PO_4$, 7 g/L of xylose and a range of 10 to 40 g/L of synthetic acetone was used to evaluate the tolerance to this product. A wild-type K12 strain of *E. coli* was grown in a 15 mL tube containing no acetone overnight at 37° C. and 200 rpm. This grown culture was used to inoculate a microplate containing the media with different concentrations of Acetone. The plate was incubated for 40 hours at 37° C. and 200 rpm. FIG. 2 illustrates the *E. coli* growth curve for increasing initial values of acetone. For concentrations of Acetone up to 25 g/L the growth profile is very similar to the control condition (no acetone), meaning that there's no impact on *E. coli* growth. At 40 g/L of acetone the growth of *E. coli* is completely impaired.

Example 3: In Situ Recovery of Volatile Fermentation Product

Figure 3:
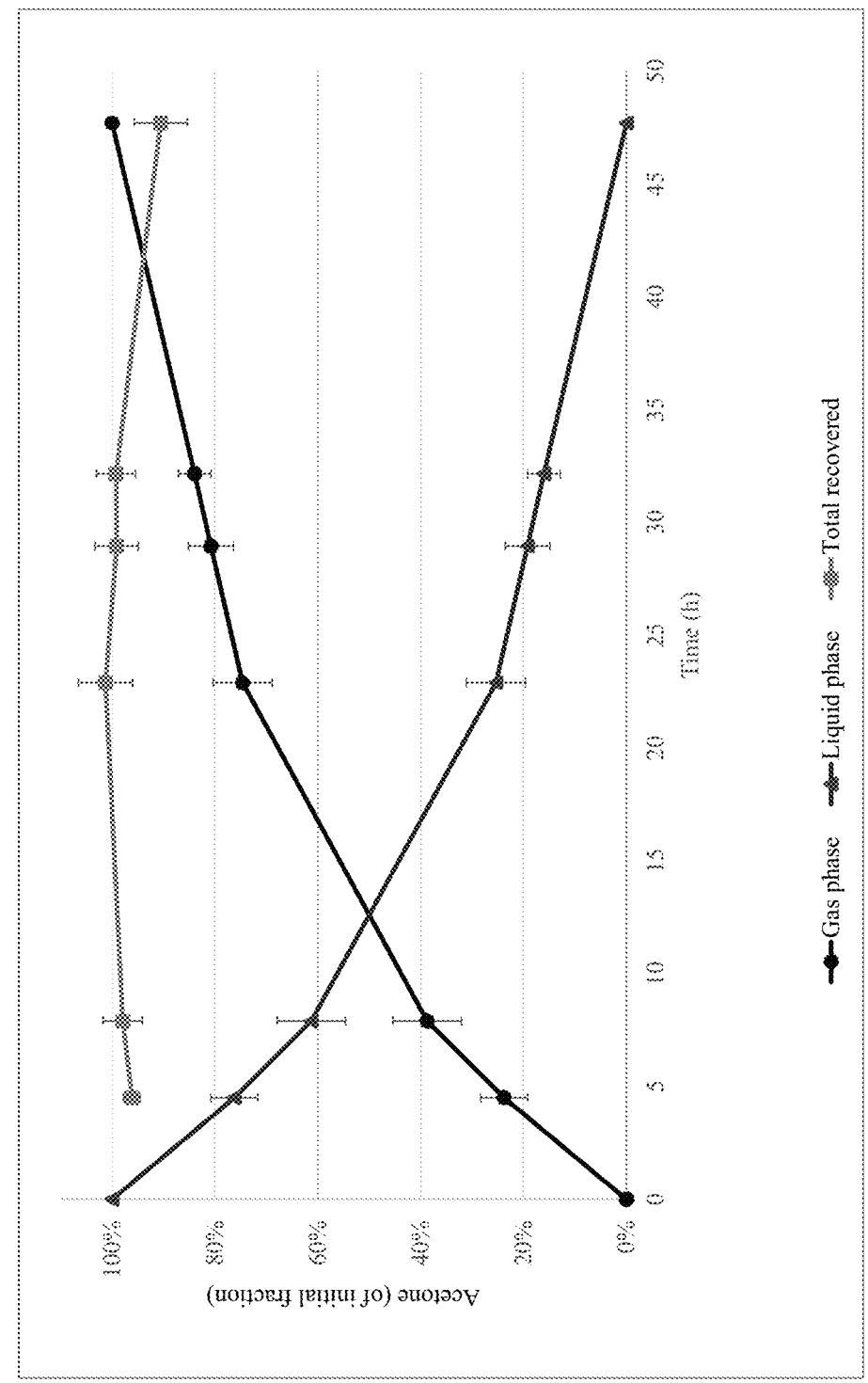
FIG. 3 shows the effect of agitation rate of acetone strip from culture broth used to alleviate *E. coli* acetone inhibition in bioreactor.

Culture media composed of 15 g/L xylose, 12 g/L tryptone, 24 g/L yeast extract, 9.4 g/L K2HPO4 and 2.2 g/L KH2PO4 and a range of 0.5 to 1 g/L synthetic acetone was used to evaluate the in situ removal of volatile products from broth. A wild strain of *E. coli* was fermented in a 1 liter bioreactor (Sartorius Stedim Biotech) at 37° C., agitation of 300 to 600 rpm and an air flow defined to provide the required OTR and the gas stripping of acetone. The product was recovered from gas phase using water traps. The analysis of the acetone fraction in the liquid phase (broth) and gas phase from FIG. 3 shows complete in situ removal from broth and high recovery in the gas phase.

Example 4: *E. Coli* Tolerance to Monoethylene Glycol (MEG)

Figure 4:
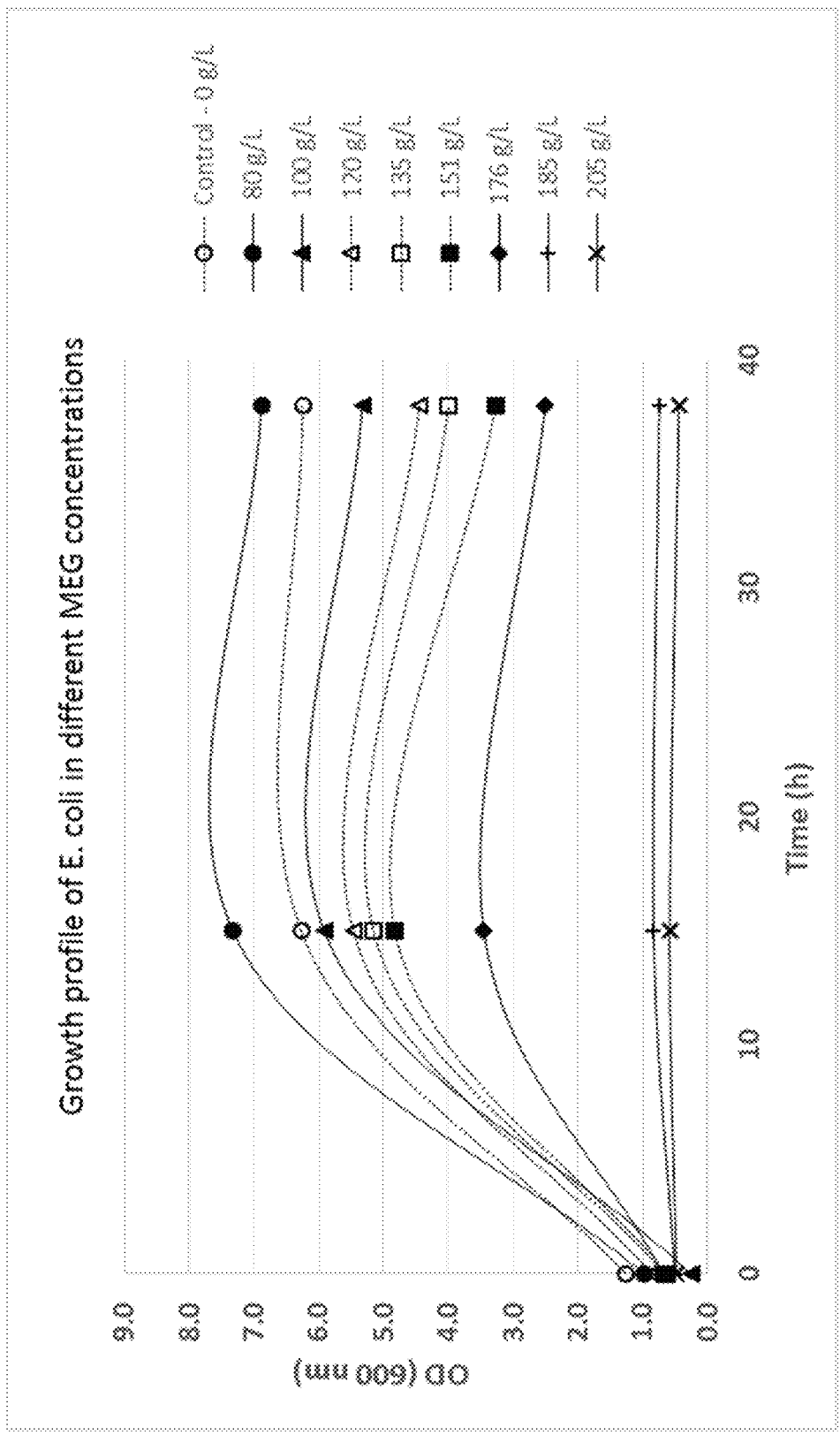
FIG. 4 illustrates the tolerance of *E. coli* grown in culture media with increasing values of monoethylene glycol (MEG) at a fixed value of acetone (ACE).

Culture media composed of 10 g/L tryptone, 5 g/L yeast extract, 5 g/L NaCl, 9.4 g/L $K_2HPO_4$, 2.2 g/L $KH_2PO_4$, 7 g/L of xylose and a range of 80 to 205 g/L of synthetic monoethylene glycol was used to evaluate the tolerance to this product. A wild-type K12 strain of *E. coli* was grown in a microplate for 40 hours at 37° C. and 200 rpm. FIG. 4 illustrates the *E. coli* growth curve for increasing initial values of monoethylene glycol. For concentrations of MEG up to 150 g/L the growth profile is very similar to the control condition (no MEG), meaning that there's no impact on *E. coli* growth. At 176 g/L of MEG the maximum OD reached by the strain is about 50% of the OD for the control condition, meaning that this concentration of MEG begins to affect *E. coli* metabolism. Above this value the concentration of MEG strongly affect *E. coli* cells and no growth is observed.

Example 5: One-Phase Process for MEG and Acetone Production Using a Mixed Carbon Source A recombinant *E. coli* strain containing pathways for MEG, IPA and acetone production was fermented in a 1 liter bioreactor (Sartorius Stedim Biotech) in a one-phase process using a mixture of glucose and xylose. The inoculum was grown in shake flasks overnight at 37° C., using minimal media composed by 2.2 g/L KH2PO4, 9.4 g/L K2HPO4, 1.3 g/L (NH4)2SO4, 10 mg/L thiamine, 320 mg/L EDTA-NaOH, 2 mg/L CoCl2.6H2O, 10 mg/L MnSO4.H2O, 5 mg/L CuSO4.5H2O, 2 mg/L H3BO3, 2 mg/L Na2MoO4.2H2O, 54 mg/L ZnSO4.7H2O, 1 mg/L NiSO4.6H2O, 100 mg/L citrate Fe (III), 100 mg/L CaCl2.2H2O, 0.3 g/L MgSO4.H2O, 12.85 g/L xylose and 2.15 g/L glucose.

Figure 5:
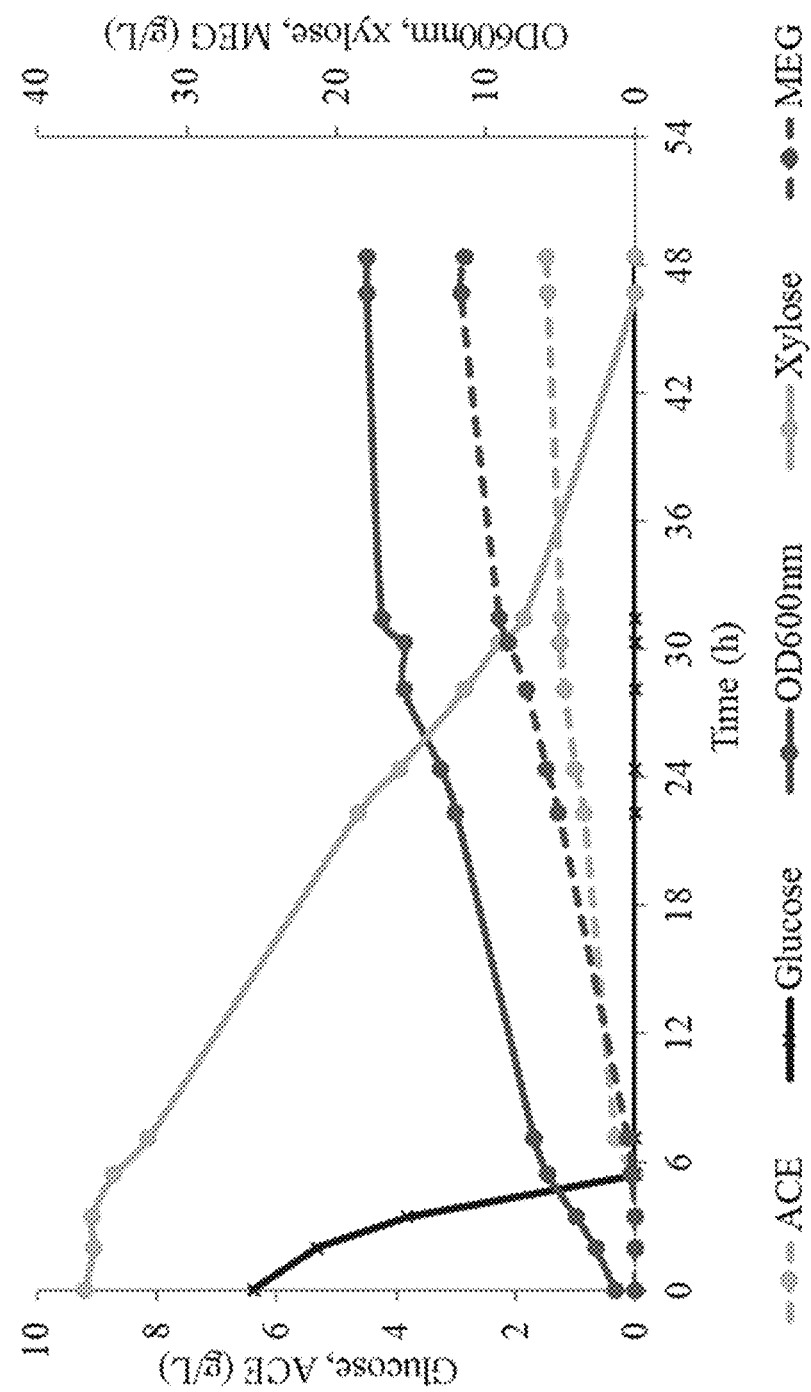
FIG. 5 describes the production of monoethylene glycol and acetone over time in a one-phase process using a recombinant *E. coli* strain.

The cells were concentrated and inoculated in the bioreactor yielding an initial concentration of 0.5 g/L of dry cell mass. The cultivation media was described above, with total initial sugar adjusted to 45 g/L while maintaining a constant relation of carbon and nitrogen. The cultivation was performed at 550 rpm, 37° C. and pH 6.5 automatically controlled using 2.5M NaOH. In situ gas stripping was performed by setting an aeration rate appropriate to supply oxygen and to strip most of acetone and IPA from fermentation broth to the bioreactor off gas. The C3 products were recovered from broth off gas by bubbling it in a sequence of three 250 mL water traps. As shown in FIG. 5, it was possible to achieve simultaneous cell growth, MEG and C3 acetone production, with a specific yield of 3 g products per g dry cell mass.

Example 6: Effect of Nutrients on Fermentation Products

Figure 6:
FIG. 6 describes the influence of C/N ratio on the simultaneous *E. coli* production of MEG and ACE.

Shake flask fermentations were performed using minimally defined media (as described in Table 2 below) and a recombinant *E. coli* strain, using different carbon to nitrogen ratios. A mixture of xylose and glucose was used as carbon source and nitrogen sulphate was used as nitrogen source. Fermentation was performed at 37° C. and 225 rpm, in erlenmeyer flasks with a designed cap capable of provide oxygen transfer and volatile products capture. The flasks were inoculated with 5 mL of an overnight culture using the same culture media, achieving an initial OD of 0.2. As shown in FIG. 6, the carbon to nitrogen ratio can influence the C3 products production, when evaluated at similar fermentation parameters.

TABLE 2

Culture media composition to tetst the effect of nutrients on fermentation products

| Component | Amount for 1 Liter |
|---|---|
| KH2PO4 | 2.2 g |
| K2HPO4 | 9.4 g |
| NaCl | 1 g |
| MgSO4•7H2O | 0.3 mg |
| Thiamine | 10 mg |
| CoCl2•6H2O | 2 mg |
| MnSO4•H2O | 10 mg |
| CuSO4•5H2O | 5 mg |
| H3BO3 | 2 mg |
| Na2MoO4•2H2O | 2 mg |
| ZnSO4•7H2O | 30 mg |
| NiSO4•6H2O | 1 mg |
| C6H5FeO7 | 100 mg |
| CaCl2•2H2O | 100 mg |

Figure 7:
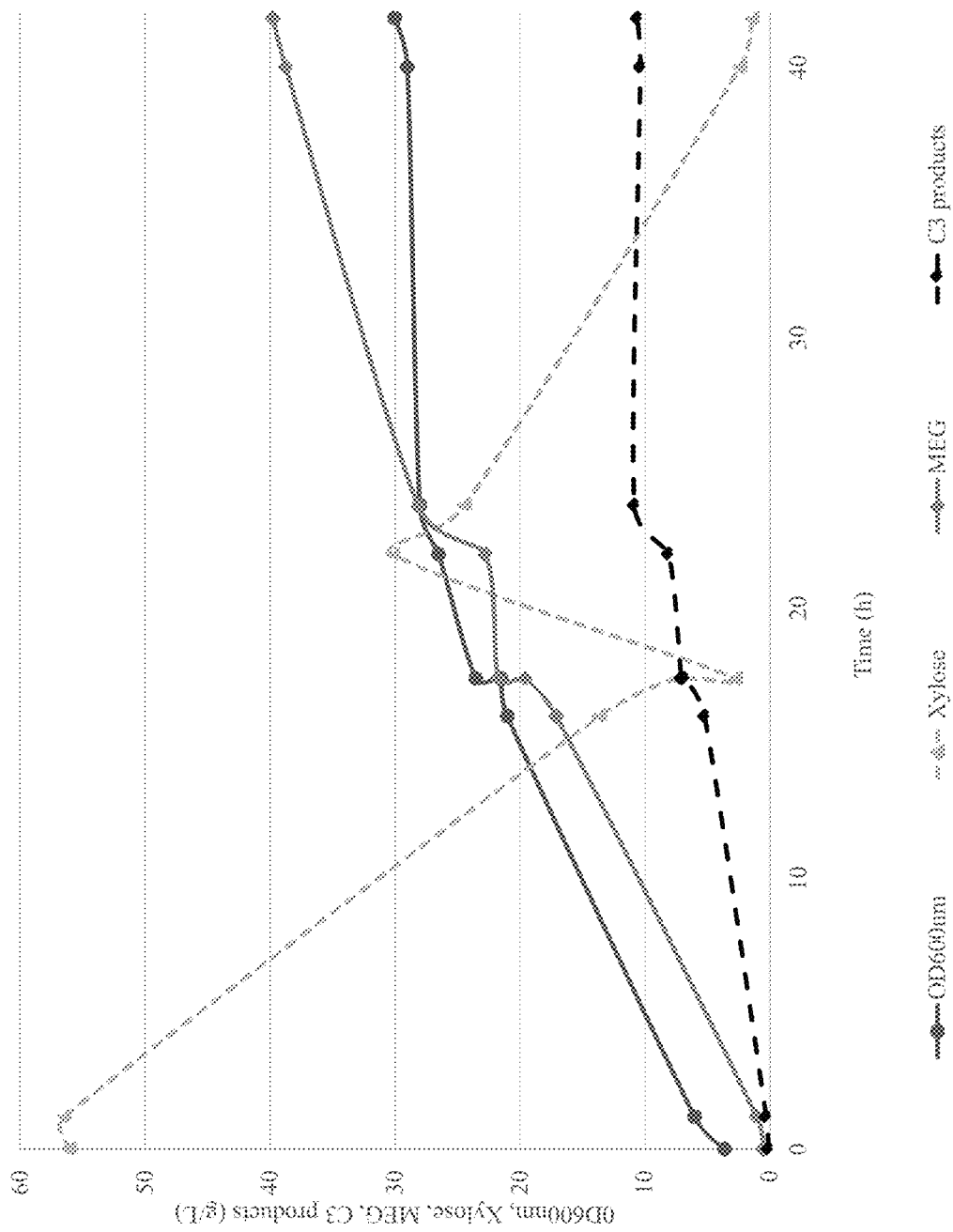
FIG. 7 describes the production of monoethylene glycol and acetone over time in a batch bioreactor with carbon pulse using a recombinant *E. coli* strain.

Example 7: Batch Fermentation with Xylose Pulse for MEG and C3 Derivative Products with High Productivities A recombinant *E. coli* strain containing pathways for MEG, IPA and acetone production was fermented in a 1 liter bioreactor (Sartorius Stedim Biotech), using media composed of 12 g/L tryptone, 24 g/L yeast extract, 9.4 g/L K2HPO4, 2.2 g/L KH2PO4 and 60 g/L xylose. Inoculum was prepared in order to achieve an initial cell concentration in the bioreactor of about of 1 g/L of dry cell weight. For this purpose, three sequential transferences were performed using culture media composed by 12 g/L tryptone, 24 g/L yeast extract, 9.4 g/L K2HPO4 and 2.2 g/L KH2PO4 and 15 g/L xylose. Cells were incubated at 37° C., 225 rpm, for 10 to 16 hours. The bioreactor inoculation was performed by centrifuging the cells and suspending the pellet in 20 mL of fresh media. The cultivation was performed at an agitation rate of 590 rpm, 37° C. and pH 7.0 automatically controlled using 5M NaOH. After carbohydrate depletion, a xylose pulse was performed in order to achieve 30 g/L in the fermenter. In situ gas stripping was performed by setting an aeration rate appropriate to supply oxygen and to strip most of acetone and IPA from fermentation broth to the bioreactor off gas. The C3 products were recovered from broth off gas by bubbling it in a sequence of three 250 mL water traps. As shown in FIG. 7, it was possible to achieve a coproducts productivity higher than 1 g/L·h.

Figure 8:
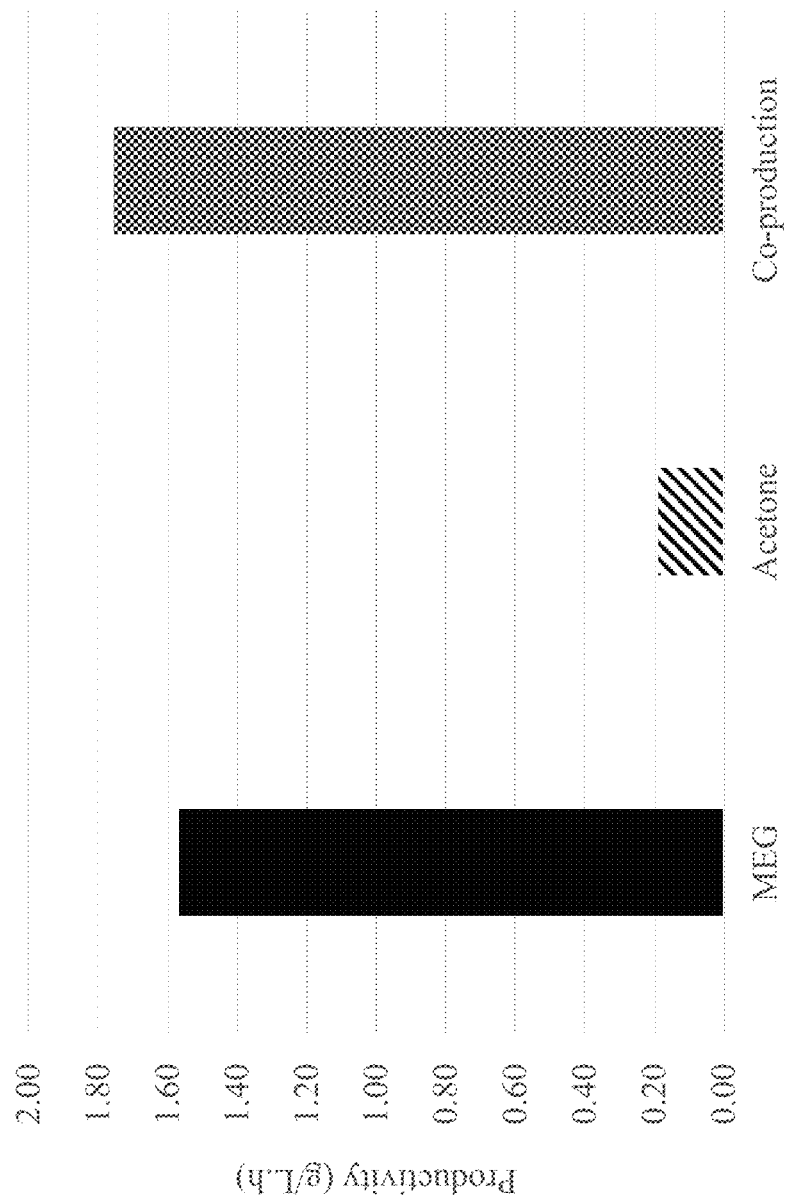
FIG. 8 illustrates the production of monoethylene glycol and acetone in a fed-batch bioreactor using a recombinant *E. coli* strain.

Example 8: Fed-Batch Fermentation in Two Stages for MEG and Acetone Production at High Productivities A recombinant E. coli strain containing pathways for MEG, IPA and acetone production was fermented in a 1 liter bioreactor (Sartorius Stedim Biotech) in two stages: first a growth phase in glucose to produce biomass followed by a production phase in xylose for the production of MEG and acetone. The medium used is composed of 2.2 g·L$^{-1}$ KH$_2$PO$_4$, 9.4 g·L$^{-1}$ K$_2$HPO$_4$, 1 g·L$^{-1}$ NaCl, 1.3 g·L$^{-1}$ (NH$_4$)$_2$SO$_4$, 10 mg·L$^{-1}$ thiamine, 320 mg·L$^{-1}$ EDTA-NaOH, 2 mg·L$^{-1}$ CoCl$_2$.6H$_2$O, 10 mg·L$^{-1}$ MnSO$_4$.H$_2$O, 5 mg·L$^{-1}$ CuSO$_4$.5H$_2$O, 2 mg·L$^{-1}$ H$_3$BO$_3$, 2 mg·L$^{-1}$ Na$_2$MoO$_4$.2H$_2$O, 54 mg·L$^{-1}$ ZnSO$_4$.7H$_2$O, 1 mg·L$^{-1}$ NiSO$_4$.6H$_2$O, 100 mg·L$^{-1}$ citrate Fe (III), 100 mg·L$^{-1}$ CaCl$_2$.2H$_2$O and 0.3 g·L$^{-1}$ MgSO$_4$.H$_2$O. Inoculum was prepared in shake flask, overnight at 37° C. in the medium described above. The cells were concentrated and inoculated in the bioreactor yielding an initial concentration of 0.1 g/L of dry cell mass. In order to achieve a high concentration of cells for the production phase an initial growth phase was performed with glucose as carbon source. Glucose was fed at the reactor in pulses of 15 g/L until a 15 g/L of dry cell mass concentration was reached maintaining a dissolved O$_2$ concentration around 30% of saturation. Nitrogen was supplemented during growth phase by the addition of NH$_4$OH 6% for pH control. The production phase was performed in xylose that was continuously fed to the reactor at 0.1 g/min. During this phase dissolved oxygen was used as the limiting factor for increased production. Temperature was controlled at 37° C. and pH at 7. During the production phase MEG was kept in the reactor and in order to decrease inhibitory effects 30% of the acetone was stripped from the reactor and recovered in adjacent traps. After 13 h of production phase 20.3 g/L of MEG and 3.2 g/L of acetone were produced at a global yield of 68% of maximum theoretical yield of co-products. As shown in FIG. 8, it was possible to achieve a coproducts productivity of 1.8 g/L·h.

Figure 9:
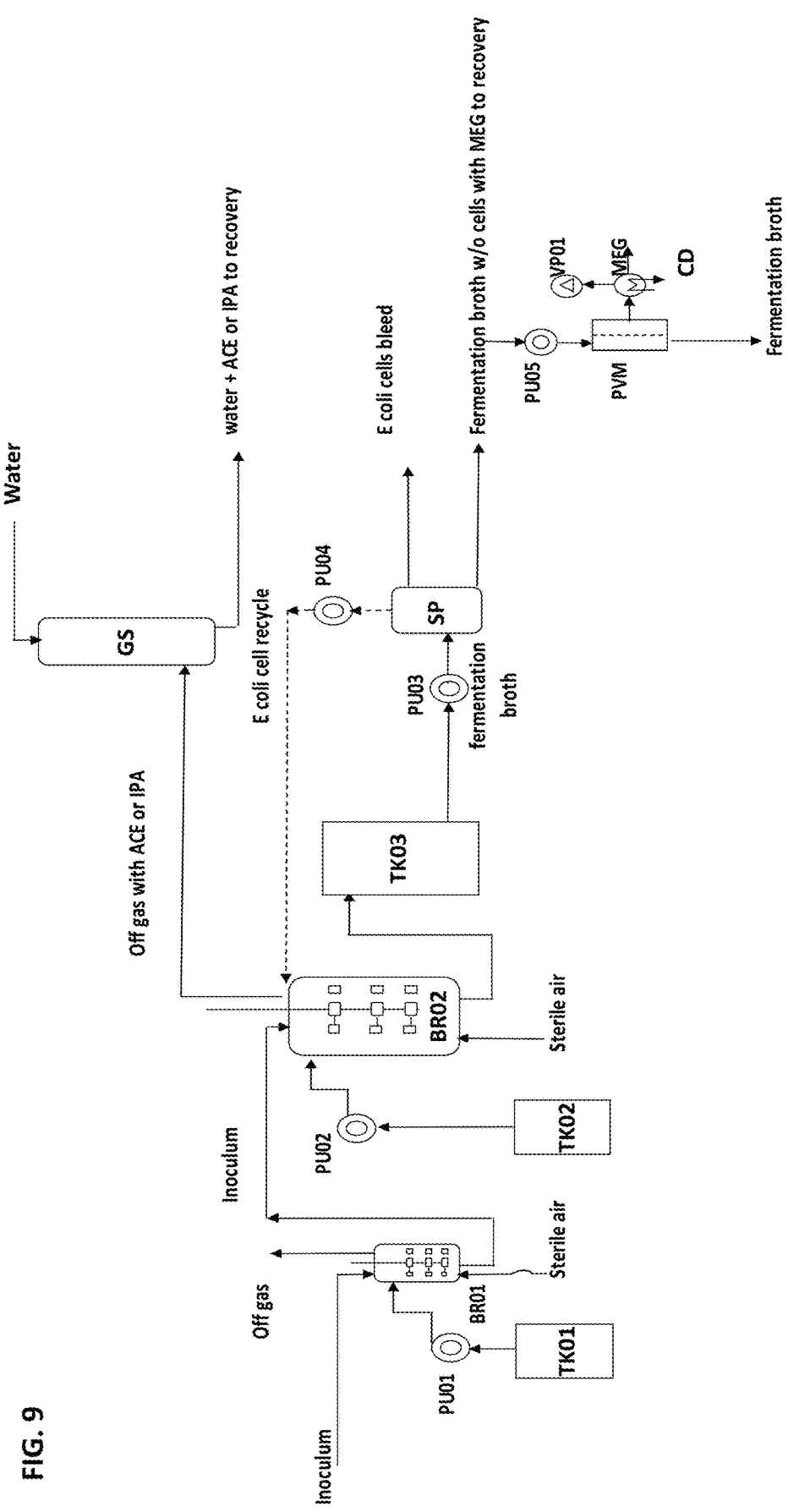
FIG. 9 illustrates the workflow process diagram for simultaneous production of monoethylene glycol, acetone, and isopropanol (IPA) and propene. Legend: BR01—bioreactor for propagation phase, BR02—bioreactor for production phase, TK—storage tank for sterile culture media, MF—microfiltration modules for cell separation, GS—gas scrubber for off gas washing and ACE/IPA recovery, PVM—pervaporation modules for product recovery, PU01 to PU06—pumps for culture media and fermentation broth flow, VP01—vacuum pump for PVM modules, CD—condenser for PVM modules.

Example 9: Process Flow for MEG, ACE, IPA and Propene Production Utilizing the Two-Phase Process In FIG. 9, BR01 stands for bioreactor for growth phase; BR02 for bioreactor for production phase; TK01, TK02 for storage tanks for sterile culture media, respectively; SP for microfiltration or centrifuge for cell separation; GS for gas scrubber for off-gas water washing and ACE/IPA recovery; PVM for pervaporation module for product recovery; PU01 to PU05 for pumps for culture media and fermentation broth flow; VP01 for vacuum pump of PVM module; and CD for condenser of PVM module. Culture media MM for the growth phase and production phase are prepared in tanks TK01 and TK02 (storage tanks for sterile culture media). Culture conditions in bioreactor BR01 (bioreactor for propagation phase) are adjusted to promote E. coli growth. BR01 is inoculated with a culture of E. coli. Culture media MM, prepared to promote E. coli growth, is pumped to BR01 from TK01 using pump PU01. Bioreactor BR02 culture conditions are adjusted for MEG, ACE and IPA production. After E. coli growth is accomplished in BR01, the produced cell mass is transferred to BR02. Culture media MM prepared for MEG, ACE and IPA production as described is pumped to BR02 from TK02 using pump PU02.

During BR02 production phase, the majority of the produced acetone (ACE) and isopropanol (IPA) are in situ removed from the fermentation broth and leave BR02 with the bioreactor off gas stream. They are properly recovered in the water gas scrubber apparatus GS. Afterwards the ACE and/or IPA solutions are directed to the recovery purification area. At the end of production phase production, the fermented broth is discharged to a holding tank TK03 and E. coli cells are separated from fermentation broth with the aid of a centrifuge or microfiltration apparatus SP. The remaining E. coli cells are removed from the system, using a known methodology, and properly discharged. Alternatively, the cells can be partially recycled to the growth phase occurring in bioreactor BR01. Remaining crude MEG solution, without E. coli cells from the SP apparatus, is then directed to the recovery purification area. Alternatively, in situ MEG removal may take place in the pervaporation module PVM.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

While the disclosure is divided into sections, subsections, and further delineations, this is simply for exemplary purposes and is in no way intended to limit the methods, processes, compositions, products, substrates, media, and the like for use in any other aspect of the disclosure. For example, the disclosure of substrates used in the fermentation phase subsection does not limit the use of the substrates to fermentation phase processes.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

Additional Embodiments

1. A biological process for producing two or more desirable products simultaneously, the process comprising:
(a) providing to at least one bioreactor one or more recombinant microorganisms engineered to express one or more enzymes from one or more biosynthesis pathways selected from a monoethylene glycol (MEG) biosynthesis pathway and one or more C3 compound biosynthesis pathways;
(b) cultivating the one or more recombinant microorganisms from (a) in one or more stages in a culture medium containing a feedstock comprising one or more substrates comprising C5 carbohydrates, C6 carbohydrates, and/or disaccharides;
(c) fermenting the culture in one or more stages under aerobic, microaerobic and/or anaerobic conditions; and
(d) recovering from the bioreactor MEG and at least one second desirable product from (c) selected from the group consisting of acetone, isopropanol, propene, precursors thereof, and mixtures thereof; wherein the at least one second desirable product is recovered continuously prior to exhaustion of the one or more substrates.

2. A biological process for producing two or more desirable products simultaneously, the process comprising:
(a) providing to at least one bioreactor one or more recombinant microorganisms engineered to express one or more enzymes from one or more biosynthesis pathways selected from a monoethylene glycol (MEG) biosynthesis pathway and one or more C3 compound biosynthesis pathways;
(b) cultivating the one or more recombinant microorganism from (a) in one or more stages in a culture medium containing a feedstock comprising one or more substrates comprising C5 carbohydrates, C6 carbohydrates, and/or disaccharides;
(c) fermenting the culture in one or more stages under aerobic, microaerobic and/or anaerobic conditions; and
(d) recovering from the bioreactor the MEG and at least one second desirable product from (c) selected from the group consisting of acetone, isopropanol, propene, precursors thereof, and mixtures thereof;
wherein the at least one second desirable product is recovered from the bioreactor two or more times prior to exhaustion of the one or more substrates.

3. A biological process for producing two or more desirable products simultaneously, the process comprising:
(a) providing to at least one bioreactor one or more recombinant microorganisms engineered to express one or more enzymes from one or more biosynthesis pathways selected from a monoethylene glycol (MEG) biosynthesis pathway and one or more C3 compound biosynthesis pathways;
(b) cultivating the one or more recombinant microorganisms from (a) in a culture medium containing a feedstock comprising one or more substrates comprising C5 carbohydrates, C6 carbohydrates, and/or disaccharides;
(c) fermenting the culture under aerobic, microaerobic and/or anaerobic conditions; and
(d) recovering from the bioreactor MEG and at least one second desirable product from (c) selected from the group consisting of acetone, isopropanol, propene, precursors thereof, and mixtures thereof;
wherein the at least one second desirable product is recovered from the bioreactor continuously prior to exhaustion of the one or more substrates; and wherein (b) and (c) occur together in the same stage.

4. A biological process for producing two or more desirable products simultaneously, the process comprising:
(a) providing to at least one bioreactor one or more recombinant microorganisms engineered to express one or more enzymes from one or more biosynthesis pathways selected from a monoethylene glycol (MEG) biosynthesis pathway and one or more C3 compound biosynthesis pathways;
(b) cultivating the one or more recombinant microorganisms from (a) in a culture medium containing a feedstock comprising one or more substrates comprising C5 carbohydrates, C6 carbohydrates, and/or disaccharides;
(c) fermenting the culture under aerobic, microaerobic and/or anaerobic conditions; and (d) recovering from the bioreactor in one or more stages MEG and at least one second desirable product from (c) selected from the group consisting of acetone, isopropanol, propene, precursors thereof, and mixtures thereof;
wherein the at least one second desirable product is recovered from the bioreactor continuously prior to exhaustion of the one or more substrates; and wherein (b) and (c) occur in separate stages.

5. The process of any one of embodiments 1-4, wherein the one or more recombinant microorganisms are engineered to express at least one enzyme selected from the group consisting of: D-tagatose 3-epimerase, D-ribulokinase D-ribulose-1-phosphate aldolase, glycolaldehyde reductase, thiolase, acetate:acetoacetyl-CoA transferase, acetoacetate decarboxylase, D-xylulose 1-kinase, D-xylulose-1-phosphate aldolase, xylose isomerase, xylose reductase, xylitol dehydrogenase, xylose dehydrogenase, xylonolactonase, xylonate dehydratase, 2-keto-3-deoxy-D-pentonate aldolase, secondary alcohol dehydrogenase, dehydratase, and a functionally equivalent variant of any one or more thereof.

6. The process of any one of embodiments 1-4, wherein the one or more recombinant microorganisms are derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis* and *Terrisporobacter glycolicus*.

7. The process of embodiment 6, wherein the one or more recombinant microorganisms are acetogenic.

8. The process of any one of embodiments 1-4, wherein the one or more C3 compound biosynthesis pathways are selected from the group consisting of: an acetone biosynthesis pathway, an isopropanol biosynthesis pathway, and a propene biosynthesis pathway.

9. The process of any one of embodiments 1-4, wherein the one or more substrates are C5 carbohydrates selected from the group consisting of xylose, arabinose, lyxose, ribose, ribulose, and xylulose.

10. The process of any one of embodiments 1-4, wherein the one or more substrates are C6 carbohydrates selected from the group consisting of glucose, mannose, fructose, allose, gulose, idose, galactose, talose, sorbose, tagatose, and psicose.

11. The process of any one of embodiments 1-4, wherein the one or more substrates are disaccharides selected from the group consisting of sucrose, lactose, lactulose, maltose, trehalose, cellobiose, and chitobiose.

12. The process of any one of embodiments 1-4, wherein the one or more substrates comprise C5 carbohydrates and C6 carbohydrates in a ratio of 20:1 to 1:20.

13. The process of any one of embodiments 1-4, wherein the one or more desired products is selected from the group consisting of MEG, acetone, isopropanol, and propene.

14. The process of any one of embodiments 1-4, wherein the cultivating and fermenting steps occur in in the same stage.

15. The process of any one of embodiments 1-4, wherein the cultivating and fermenting steps occur in separate stages.

16. The process of any one of embodiments 1-4, wherein the cultivating and fermenting steps occur in separate bioreactors.

17. The process of any one of embodiments 1-4, wherein the cultivating and fermenting steps occurs in the same bioreactor.

18. The process of embodiment 11, wherein the bioreactor operates under aerobic, microaerobic, or anaerobic conditions; or a combination thereof.

19. The process of any one of the preceding embodiments, wherein a first stage of the cultivation operate under aerobic or microaerobic conditions, and any subsequent stages operate under aerobic, microaerobic, or anaerobic conditions.

20. The process of embodiment 11, wherein the one or more stages of (c) receive the culture and/or culture media as a batch, a fed-batch, or a continuous mode feed.

21. The process of any one of the preceding embodiments, wherein the cultivating stage receives the culture and/or culture media as a batch, a fed-batch, or a continuous mode feed, and any subsequent stages operate as a batch, a fed-batch, or a continuous mode feed.

22. The process of embodiment 16, wherein the cultivation step occurs in a different type of bioreactor than the subsequent step.

23. The process of embodiment 16, wherein the cultivation step occurs in the same type of bioreactor as the subsequent step.

24. The process of any one of embodiments 1-4, wherein an additional feedstock comprising a gaseous substrate is provided to the bioreactor.

25. The process of embodiment 24, wherein the gaseous substrate comprises hydrogen gas, carbon monoxide, carbon dioxide, or combinations thereof.

26. The process of any one of embodiments 1-4, wherein the acetone, isopropanol, and/or propene are produced, and wherein said acetone, isopropanol, and/or propene, or a mixture thereof are recovered from the bioreactor continuously in situ.

27. The process of any one of embodiments 1-4, wherein (b) occurs prior to (c); or wherein (b) and (c) occur concurrently.

28. The process of any one of embodiments 1-4, wherein the at least one second desirable product recovered are acetone and/or isopropanol.

29. The process of embodiment 28, wherein acetone, isopropanol, and/or MEG, in total, are produced in an amount at least about 2 kg/m$^3$ per hour.

30. The process of embodiment 28, wherein a concentration of acetone, isopropanol, and/or MEG produced is at least about 40 g/L.

31. The process of embodiment 15, wherein oxygen concentration in the cultivating step is adjusted to a range of 1% to 50% of oxygen dissolved in the medium.

32. The process of embodiment 15, wherein a total amount of the one or more substrates that are provided to the cultivating step ranges from about 10 kg/m$^3$ to about 500 kg/m$^3$.

33. The process of embodiment 14, wherein the culture medium comprises carbon (C) that is provided from C5 carbohydrates, C6 carbohydrates, and/or disaccharides.

34. The process of embodiment 14, wherein the culture medium comprises essential nutrients including nitrogen (N), phosphorus (P), magnesium (Mg), and iron (Fe).

35. The process of embodiment 15, wherein a ratio of C:N in the cultivating step is at least 10:1.

36. The process of embodiment 15, wherein a ratio of C:P in the cultivating step is at least 5:1.

37. The process of embodiment 15, wherein a ratio of C:Mg in the cultivating step is at least 50:1.

38. The process of embodiment 15, wherein a ratio of C:Fe in the cultivating step is at least 300:1.

39. The process of embodiment 15, wherein the final concentration of cell mass of the one or more recombinant microorganisms in the cultivating step ranges from about 1 kg/m$^3$ to about 100 kg/m$^3$ as of a dry cell mass.

40. The process of embodiment 15, wherein the cultivating step operates from 5 up to 100 hours for the cultivation of the cells of the one or more recombinant microorganisms.

41. The process of embodiment 15, wherein the culture in the fermenting step comprises about 1% to about 30% of the cell mass, which is transferred from the cultivating step in the culture medium with the one or more substrates.

42. The process of embodiment 15, wherein the oxygen concentration in the fermenting step is adjusted to a range of 0% to 10% of dissolved oxygen in the medium.

43. The process of embodiment 15, wherein a total amount of the one or more substrates that are provided to the fermenting step ranges from about 100 kg/m$^3$ to about 800 kg/m$^3$.

44. The process of embodiment 15, wherein a ratio of C:N in the fermenting step is at least 50:1.

45. The process of embodiment 15 wherein a ratio of C:P in the fermenting step is at least 20:1.

46. The process of embodiment 15, wherein a ratio of C:Mg in the fermenting step is at least 200:1.

47. The process of embodiment 15, wherein a ratio of C:Fe in the fermenting step is at least 800:1.

48. The process of embodiment 15, wherein the fermenting step operates from 10 up to 300 hours for fed-batch operation and up to 300 hours for continuous operation.

49. The process of embodiment 15, wherein a total amount of the one or more substrates that are provided to the bioreactor ranges from about 100 kg/m$^3$ to about 800 kg/m$^3$.

50. The process of embodiment 14, wherein a ratio of C:N in the bioreactor is at least 10:1.

51. The process of embodiment 14, wherein a ratio of C:P in the in the bioreactor is at least 5:1.

52. The process of embodiment 14, wherein a ratio of C:Mg in the in the bioreactor is at least 50:1.

53. The process of embodiment 14, wherein a ratio of C:Fe in the in the bioreactor is at least 300:1.

54. The process of embodiment 14, wherein the the bioreactor operates between 10 and 300 hours.

55. The process of embodiment 14 or 15, wherein the desirable products that are recovered from the fermenting step are acetone, isopropanol, MEG, and/or propene.

56. The process of embodiment 14 or 15, wherein acetone is produced at least about 20 kg/m$^3$.

57. The process of embodiment 14 or 15, wherein isopropanol is produced at least about 35 kg/m$^3$.

58. The process of embodiment 14 or 15, wherein MEG is produced at least about 100 kg/m$^3$.

59. The process of any one of embodiments 1-4, 14, or 15, wherein the process further comprises removing acetone and/or isopropanol from the fermentation broth in situ.

60. The process of any one of embodiments 1-4, wherein three or more desirable products are produced simultaneously.

What is claimed is:

1. A biological process for producing monoethylene glycol (MEG) and a second desirable product simultaneously, the process comprising:
    (a) providing a recombinant microorganism in a bioreactor, the recombinant microorganism being engineered to express one or more enzymes from a MEG biosynthesis pathway, a C3 compound biosynthesis pathway, or both;
    (b) cultivating the recombinant microorganism in a culture medium containing a feedstock comprising a substrate comprising C5 carbohydrates, C6 carbohydrates, and/or disaccharides;
    (c) fermenting the recombinant microorganism under aerobic, microaerobic and/or anaerobic conditions; and
    (d) recovering MEG and the second desirable product from the bioreactor, wherein the second desirable product is selected from the group consisting of acetone, isopropanol, propene, precursors thereof, and mixtures thereof;
    wherein the second desirable product is recovered continuously prior to exhaustion of the substrate;
    wherein the enzymes from the MEG and C3 compound biosynthesis pathways are selected from D-tagatose 3-epimerase, D-ribulokinase, D-ribulose-1-phosphate aldolase, glycolaldehyde reductase, thiolase, acetate:acetoacetyl-CoA transferase, acetoacetate decarboxylase, D-xylulose 1-kinase, D-xylulose-1-phosphate aldolase, xylose isomerase, xylose reductase, xylitol dehydrogenase, xylose dehydrogenase, xylonolactonase, xylonate dehydratase, 2-keto-3-deoxy-D-pentonate aldolase, secondary alcohol dehydrogenase, dehydratase, or a functionally equivalent variant having at least 80% amino acid identity of any one thereof.

2. The process of claim 1, wherein the recombinant microorganism is derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis* and *Terrisporobacter glycolicus*.

3. The process of claim 1, wherein the C3 compound biosynthesis pathway is selected from the group consisting of: an acetone biosynthesis pathway, an isopropanol biosynthesis pathway, and a propene biosynthesis pathway.

4. The process of claim 1, wherein the substrate is a C5 carbohydrate selected from the group consisting of xylose, arabinose, lyxose, ribose, ribulose, xylulose, and combinations thereof.

5. The process of claim 1, wherein the substrate is a C6 carbohydrate selected from the group consisting of glucose, mannose, fructose, allose, gulose, idose, galactose, talose, sorbose, tagatose, psicose, and combinations thereof.

6. The process of claim 1, wherein the substrate is a disaccharide selected from the group consisting of sucrose, lactose, lactulose, maltose, trehalose, cellobiose, chitobiose, and combinations thereof.

7. The process of claim 1, wherein the second desirable product is selected from the group consisting of acetone, isopropanol, and propene.

8. The process of claim 1, wherein the cultivating and fermenting steps occur simultaneously in a single stage.

9. The process of claim 1, wherein the cultivating and fermenting steps occur in separate stages.

10. The process of claim 1, wherein a first stage of the cultivation operates under aerobic or microaerobic conditions, and any subsequent stages of the cultivation and fermentation operate under aerobic, microaerobic, or anaerobic conditions.

11. The process of claim 1, wherein acetone, isopropanol, and/or propene are produced, and wherein said acetone, isopropanol, and/or propene, or a mixture thereof, are recovered from the bioreactor continuously in situ.

12. The process of claim 1, wherein (b) occurs prior to (c); or wherein (b) and (c) occur concurrently.

13. The process of claim 1, wherein a concentration of acetone, isopropanol, and/or MEG produced is at least about 40 g/L.

14. The process of claim 1, wherein acetone is produced at least about 20 kg/m$^3$.

15. The process of claim 1, wherein isopropanol is produced at least about 35 kg/m$^3$.

16. The process of claim 1, wherein MEG is produced at least about 100 kg/m$^3$.

17. The process of claim 1, wherein the process further comprises removing acetone and/or isopropanol from the bioreactor in situ.

* * * * *